United States Patent
Kwong et al.

(10) Patent No.: US 7,993,763 B2
(45) Date of Patent: Aug. 9, 2011

(54) ORGANOMETALLIC COMPOUNDS HAVING HOST AND DOPANT FUNCTIONALITIES

(75) Inventors: Raymond Kwong, Plainsboro, NJ (US); Chuanjun Xia, Lawrenceville, NJ (US); Jason Brooks, Philadelphia, PA (US)

(73) Assignee: Universal Display Corporation, Ewing, NJ (US)

( * ) Notice: Subject to any disclaimer, the term of this patent is extended or adjusted under 35 U.S.C. 154(b) by 1021 days.

(21) Appl. No.: 11/798,115

(22) Filed: May 10, 2007

(65) Prior Publication Data

US 2008/0280163 A1    Nov. 13, 2008

(51) Int. Cl.
    B32B 9/04    (2006.01)
    B05D 5/12   (2006.01)
    C07F 17/02  (2006.01)

(52) U.S. Cl. .................. 428/704; 427/126.1; 546/10

(58) Field of Classification Search .................. 428/690, 428/917; 313/504, 506; 257/40, E51.044; 546/4, 10; 427/66
See application file for complete search history.

(56) References Cited

U.S. PATENT DOCUMENTS

| | | |
|---|---|---|
| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,310,360 B1 | 10/2001 | Forrest |
| 6,337,102 B1 | 1/2002 | Forrest et al. |
| 6,468,819 B1 | 10/2002 | Kim et al. |
| 6,548,956 B2 | 4/2003 | Forrest et al. |
| 6,576,134 B1 | 6/2003 | Agner |
| 6,602,540 B2 | 8/2003 | Gu et al. |

(Continued)

FOREIGN PATENT DOCUMENTS

EP    1 659 129    5/2006

(Continued)

OTHER PUBLICATIONS

U.S. Appl. No. 10/233,470, filed Sep. 4, 2002, Forrest et al.

(Continued)

Primary Examiner — Angela Ortiz
Assistant Examiner — J. L. Yang
(74) Attorney, Agent, or Firm — Kenyon & Kenyon LLP

(57) ABSTRACT

Organometallic compounds comprising an emissive core and one or more poly-phenylene branches linked to the emissive core. Host moieties are provided as pendant groups on the branches. In some cases, the poly-phenylene chain is linked in meta configuration to reduce π-conjugation in the chain. Suitable host moieties for use in the organometallic compound include those that contain carbazole or triphenylene structures. The quantity and types of host moieties on the organometallic compound may be varied to tune the molecular weight ratio of the host moieties relative to the emissive core. In some cases, the organometallic compound is sufficiently soluble in organic solvents to permit solution processing. Also provided are organic electronic devices comprising organometallic compounds of the present invention and methods for making an organic electronic device using organometallic compounds of the present invention.

39 Claims, 8 Drawing Sheets

U.S. PATENT DOCUMENTS

| | | | |
|---|---|---|---|
| 6,830,828 | B2 | 12/2004 | Thompson et al. |
| 6,835,469 | B2 | 12/2004 | Kwong |
| 7,071,615 | B2 | 7/2006 | Lu et al. |
| 7,132,681 | B2 * | 11/2006 | Grushin et al. ............... 257/40 |
| 2002/0024293 | A1 * | 2/2002 | Igarashi et al. ............. 313/483 |
| 2002/0182441 | A1 | 12/2002 | Lamansky et al. |
| 2003/0230980 | A1 | 12/2003 | Forrest et al. |
| 2004/0133004 | A1 * | 7/2004 | Stossel et al. ................... 546/2 |
| 2004/0137263 | A1 | 7/2004 | Burn et al. |
| 2004/0239237 | A1 | 12/2004 | Matsusue |
| 2005/0116622 | A1 | 6/2005 | Lo et al. |
| 2006/0119259 | A1 | 6/2006 | Bae et al. |
| 2007/0009759 | A1 | 1/2007 | Burn et al. |
| 2008/0211391 | A1 * | 9/2008 | Burn et al. .................. 313/504 |

FOREIGN PATENT DOCUMENTS

| | | |
|---|---|---|
| GB | 2 415 960 | 1/2006 |
| JP | 2006 278651 | 10/2006 |
| JP | 2007 184348 | 7/2007 |
| WO | WO 02/074015 | 9/2002 |
| WO | WO 2005/021678 | 3/2005 |
| WO | WO 2006/001150 | 1/2006 |
| WO | WO 2006/097717 | 9/2006 |
| WO | WO 2006/129471 | 12/2006 |

OTHER PUBLICATIONS

Adachi et al., "Nearly 100% internal phosphorescence efficiency in an organic light emitting device", J. App. Phys. vol. 90 No. 10, 5048-51, Nov. 15, 2001.

Baldo et al., "Highly Efficient Phosphorescent Emission from Organic Electroluminescent Devices", Nature 395:151-154, 1998.

Baldo et al., "Very high efficiency green organic light-emitting devices based on electrophosphorescence," Appl. Phys.Lett. 75(3):4-6, 1999.

Carlise et al., 2005, "Phosphorescent Side-Chain Functionalized Poly(norbornese)s Containing Iridium Complexes", Macromolecules 38:9000-9008.

Chen et al., 2003, "High-efficiency red-light emission from polyfluorenes grafted with cyclometalated iridium complexes and charge transport moiety" J. Am. Chem Soc 125:636-637.

Ding et al., 2006, "Highly Efficient Green-Emitting Phosphorescent Iridium Dendrimers Based on Carbazole Dendrons", Adv. Funct. Mat. 16:575-81.

Evans et al., 2006, "Triplet energy back transfer in conjugated polymers with pendant phosphorescent iridium complexes", J. Am. Chem. Soc. 128:6647-6656.

Jiang et al., 2005, "High Efficiency Electrophosphorescent Fluorene-alt-carbazole Copolymers N-Grafted with Cyclometalated Ir Complexes", Macromolecules 38:4072-4080.

Li et al., 2006, "Multifunctional platinum porphyrin dendrimers as emitters in undoped phosphorescent based light emitting devices", Appl. Phys. Lett. 89:061125-1.

Lo et al., 2006, "The synthesis and properties of iridium cored dendrimers with carbazole dendrons", Organic Electronics 7:85-98.

Liu et al., 2006, "Red Phosphorescent Iridium Complex Containing Carbazole-Functionalized β-Diketonate for Highly Efficient Nondoped Organic Light Emitting Diodes", Adv. Funct. Mater. 16:1441-1448.

Robinson et al, 2000, "Synthesis, morphology and optoelectronic properties of tris[(N-ethylcarbazoly1)(3',5'-hexyloxybenzoyl)methane](phenanthroline)-europium", Chem. Commun. 1645-1646.

Sandee et al., 2004, "Solution-Processable Conjugated Electrophoshphorescent Polymers", J. Am. Chem. Soc. 126:7041-7048.

Schulz et al., 2006, "Ehnancement of Phosphorescence of Ir Complexes Bound to Conjugated Polymers: Increasing the Triplet Level of the Main Chain", Macromolecules 39:9157-9165.

Wang et al., 2006, "Polymer based Tris-(2-phenylpyridine)iridium complexes", Macromolecules 39:3140-3146.

Wong et al., 2006, "Multifunctional Iridium Complexes Based on Carbazole Modules as Highly Efficient Electrophosphors", Angew. Chem. Int. Ed. 45:7800-7803.

Wong et al., 2005, "A Multifunctional Platinum Based Triplet Emitter for OLED Applications", Organometallics 24:4079-4082.

You et al., 2006, "Blue Electrophosphorescent from Iridium Complex Covalently Bonded to the Poly(9-dodecyl-3-vinylcarbazole): Suppressed Phase Segregation and Enhanced Energy Transfer", Macromolecules 39:349-356.

Zhang et al., 2006, "Saturated Red Emitting Electorphosphorescent Polymers with Iridium Coordinating to β-Diketonate Units in the Main Chain:", Macromolec. Rapid Commun. 27:1926-1931.

Zhang et al., 2006, "Highly efficient Polymer Light Emitting Diodes using color-tunable carbazole based iridium complexes", Chem. Phys. Lett. 422:386-390.

Zhen et al., 2006, "Electrophosphorescent Chelating Copolymers Based on Linkage Isomers of Naphthylpyridine-Iridium Complexes with Fluorene", Macromolecules 39:1693-1700.

PCT International Search Report and Written Opinion from PCT/US2008/003979 mailed on Sep. 15, 2008.

Liu et al., "Monodispersed fluorescent and phosphorescent oligofluorene functionalized molecular stars: synthesis, characterization, luminescent and electroluminescent properties", Polymer Preprints, 47(2): 559-560.

* cited by examiner

ORGANOMETALLIC COMPOUNDS HAVING HOST AND DOPANT FUNCTIONALITIES

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

TECHNICAL FIELD

The present invention relates to organic electronic devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY

In one aspect, the present invention provides an organometallic compound comprising one or more branches linked to an emissive core as represented by the formula:

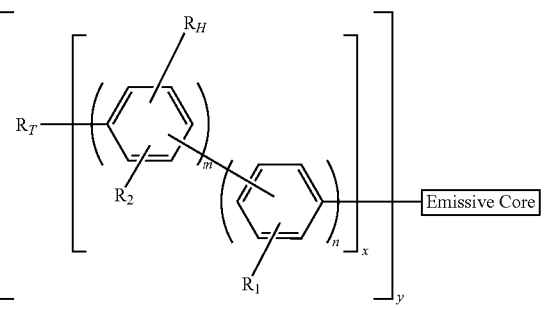

wherein the emissive core comprises a metal atom and a plurality of ligands coordinated to the metal atom; wherein each branch is linked to one of the plurality of ligands; wherein variable "y" has an integer value of 1 to 3; wherein each variable "x" independently has an integer value of at least 2; wherein each variable "n" independently has an integer value of 0 or greater; wherein each variable "m" independently has an integer value of 1 or greater; wherein each host moiety $R_H$ is independently an aryl group having at least two rings or a heteroaryl group having at least two rings; wherein each terminal group $R_T$ is independently selected from the group consisting of: an alkyl group, a heteroalkyl group, an aryl group, and a heteroaryl group; wherein each of $R_1$ and $R_2$ represents one or more independently selected substitutions located on any position of their respective rings, wherein each of the substitutions are independently selected from the group consisting of: an alkyl group, a heteroalkyl group, an aryl group, and a heteroaryl group. In some cases, each phenyl unit within the poly-phenylene chain of the branch is linked to adjacent phenyl units in meta configuration.

In another aspect, the present invention provides an organic electronic device comprising: an anode; a cathode; and a first organic layer disposed between the anode and the cathode, wherein the first organic layer comprises an organometallic compound of the present invention.

In yet another aspect, the present invention provides a method for making an organic electronic device, comprising: providing a first electrode disposed on a substrate; forming a first organic layer over the first electrode, wherein the first organic layer comprises an organometallic compound of the present invention; and forming a second electrode disposed over the first organic layer.

DETAILED DESCRIPTION

Figure 1:
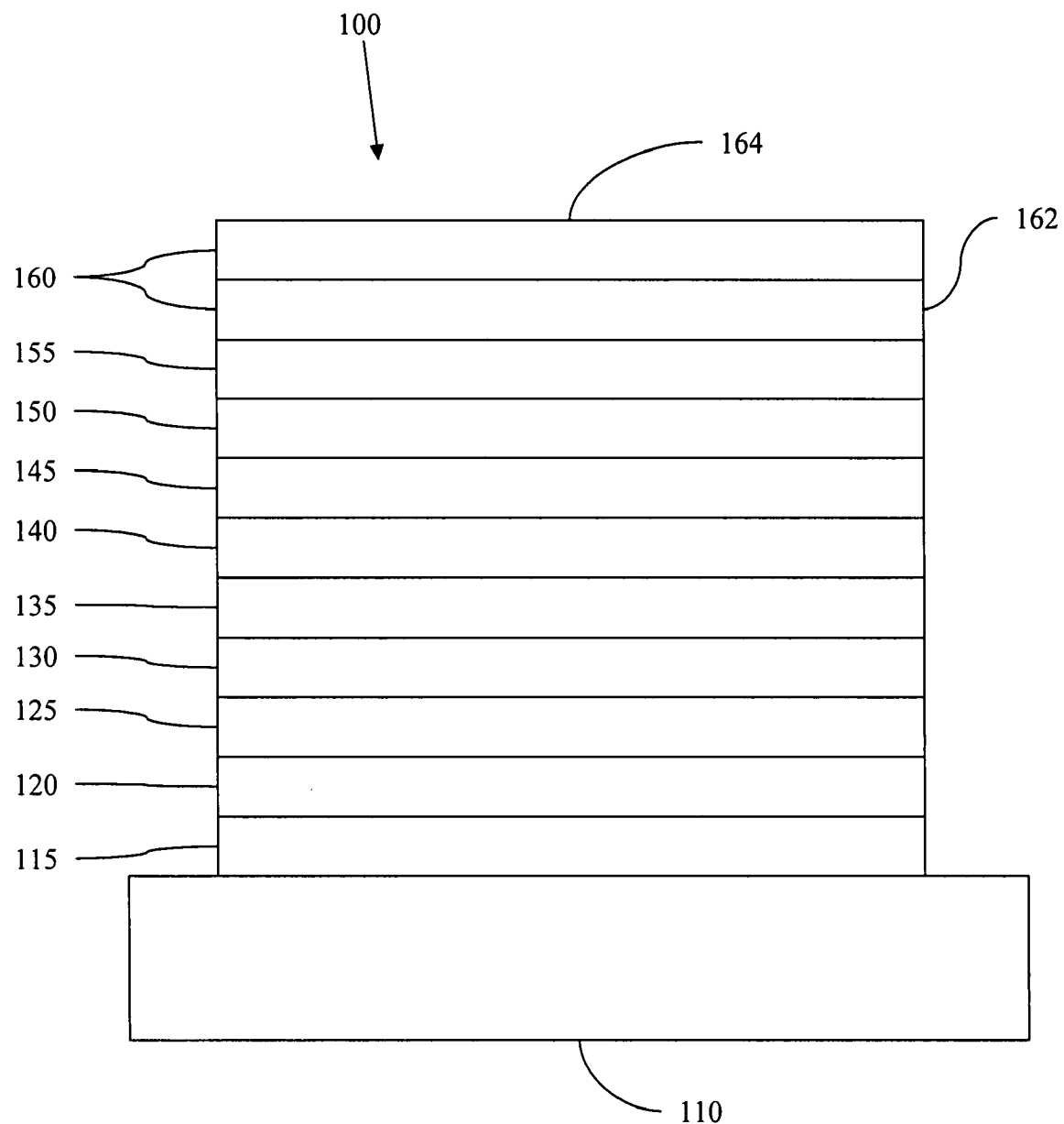
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 1, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium (III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
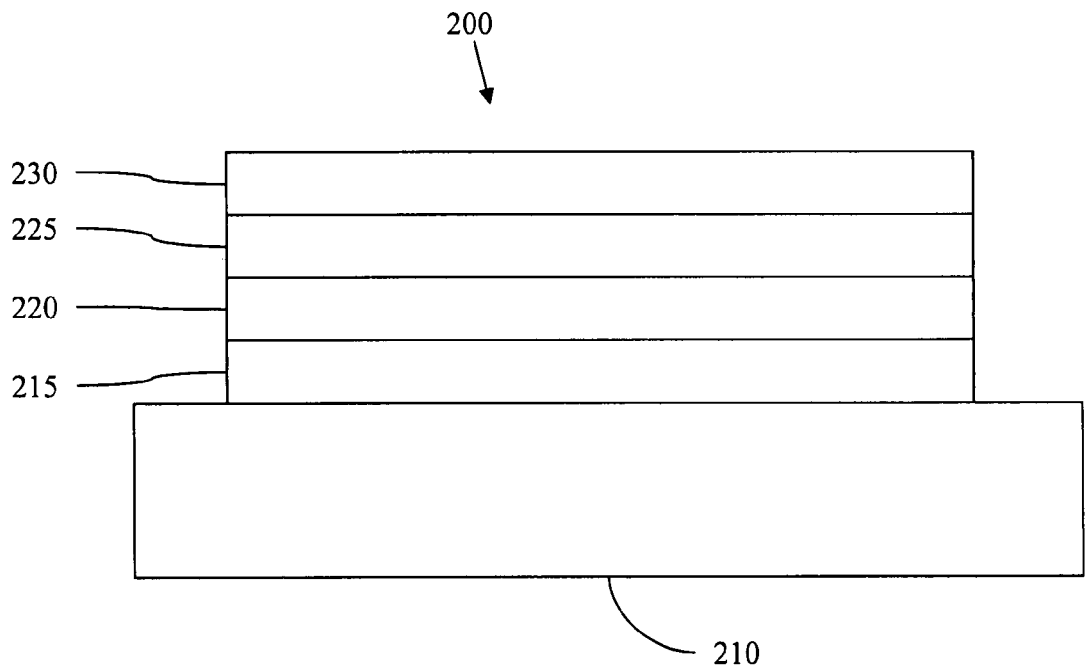
FIG. 2 shows an inverted organic light emitting device that does not have a separate electron transport layer.
Figure 3:
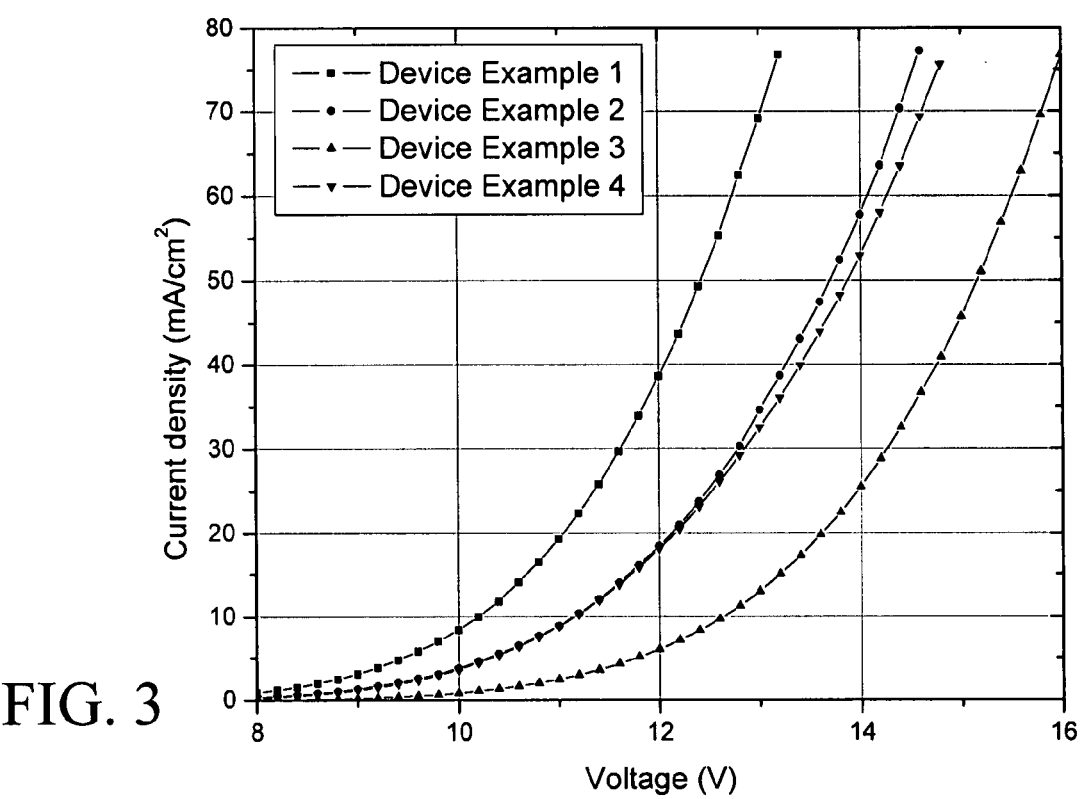
FIG. 3 shows a plot of current density v. voltage for Device Examples 1-4.
Figure 4:
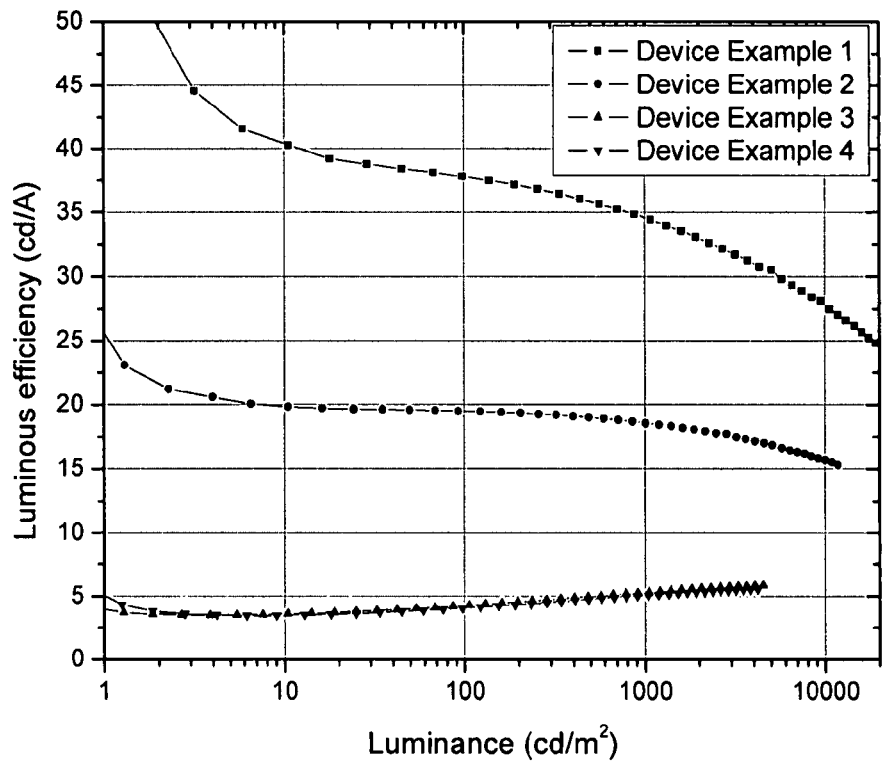
FIG. 4 shows a plot of luminous efficiency v. luminance for Device Examples 1-4.
Figure 5:
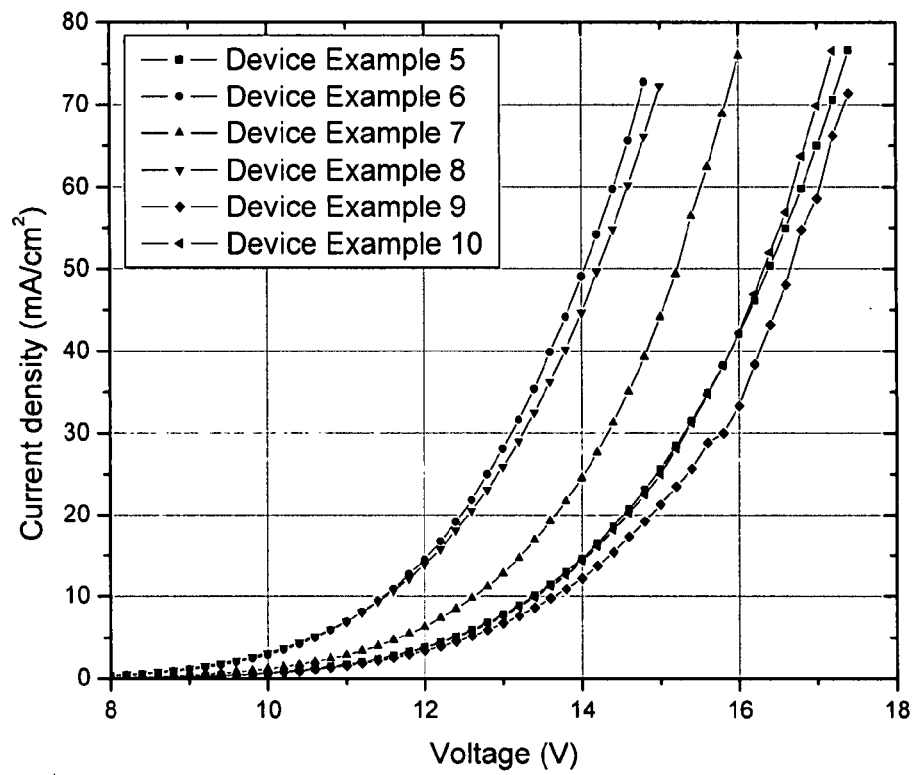
FIG. 5 shows a plot of current density v. voltage for Device Examples 5-10.
Figure 6:
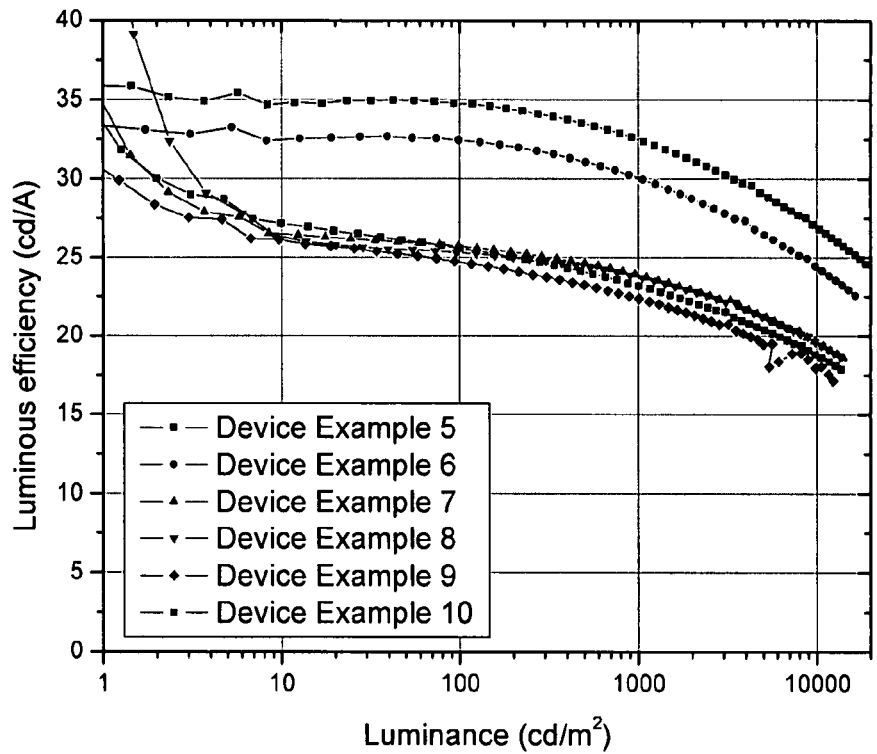
FIG. 6 shows a plot of luminous efficiency v. luminance for Device Examples 5-10.
Figure 7:
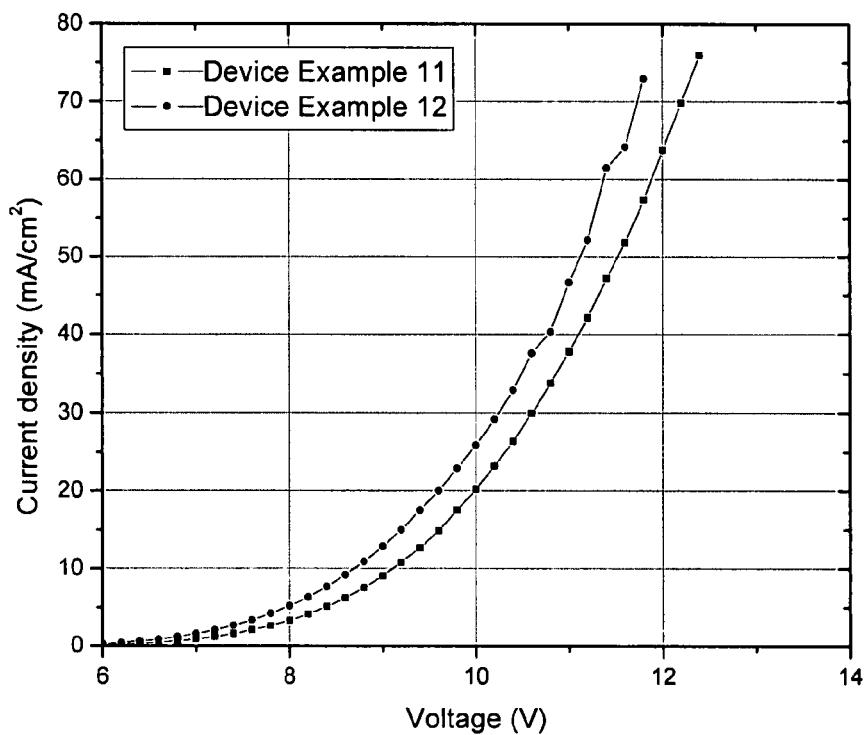
FIG. 7 shows a plot of current density v. voltage for Device Examples 11 and 12.
Figure 8:
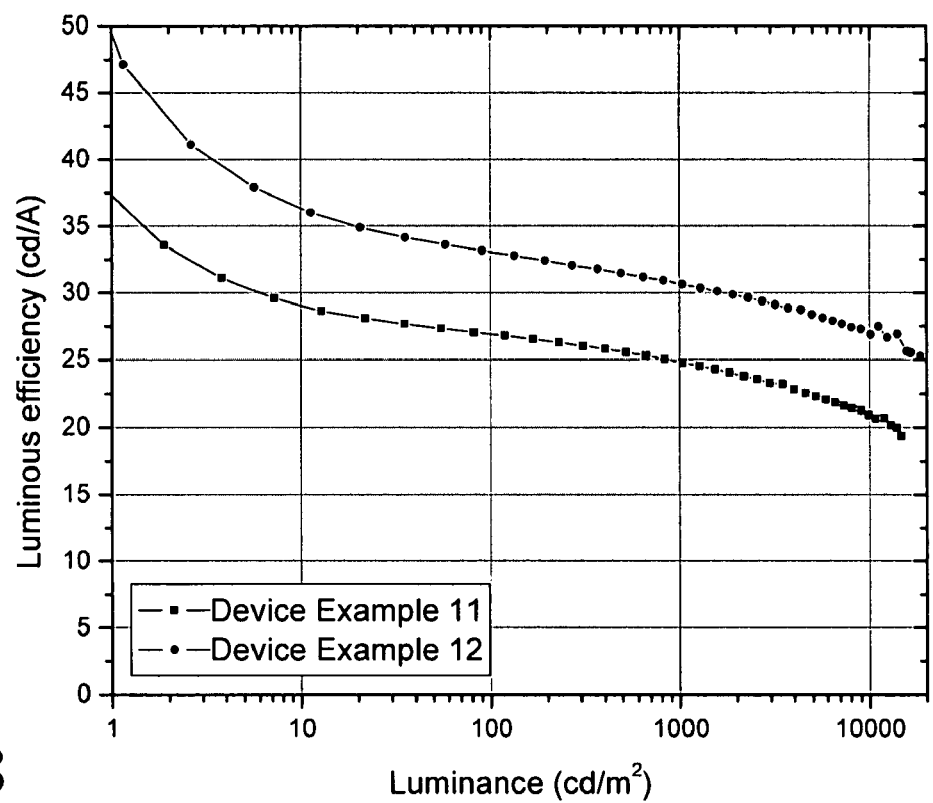
FIG. 8 shows a plot of luminous efficiency v. luminance for Device Examples 11 and 12.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, may be used in small molecules to enhance their ability to undergo solution processing. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The term "alkyl group," as used herein, refers to alkyl moieties and encompasses both straight and branched alkyl chains. In some cases, alkyl groups suitable for use as substituents in the present invention are those containing one to fifteen carbon atoms, which includes methyl, ethyl, propyl, isopropyl, butyl, isobutyl, tert-butyl, and the like. Additionally, the alkyl moieties themselves may be substituted with one or more substituents. The term "heteroalkyl group," as used herein, refers to alkyl moieties that include heteroatoms. In some cases, heteroalkyl groups suitable for use as substituents in the present invention are those containing one to fifteen carbon atoms.

The term "aryl group," as used herein, refers to aryl moieties and encompasses structures containing at least one aromatic ring, including single-ring groups as well as polycyclic ring systems. The polycyclic rings may have two or more rings in which two atoms are common by two adjoining rings (the rings are "fused") wherein at least one of the rings is aromatic. In some cases, aryl moieties suitable for use as substituents in the present invention are those that contain one to three aromatic rings, which includes phenyl, naphthyl, biphenyl, and phenanthryl.

The term "heteroaryl group," as used herein, refers to heteroaryl moieties and encompasses single ring heteroaromatic groups that may include from one to four heteroatoms. Examples of heteroaryl moieties include pyrrole, furan, thiophene, imidazole, oxazole, thiazole, triazole, tetrazole, pyrazole, pyridine, pyrazine, and pyrimidine, and the like. The term "heteroaryl" also includes polycyclic heteroaromatic systems having two or more rings in which two atoms are common to two adjoining rings (the rings are "fused") wherein at least one of the rings is a heteroaryl. The other rings can be cycloalkyls, cycloalkenyls, aryl, heterocycles, and/or heteroaryls.

In one aspect, the present invention provides an organometallic compound having host and dopant functionalities. The organometallic compound comprises one or more branches linked to an emissive core as represented by the formula:

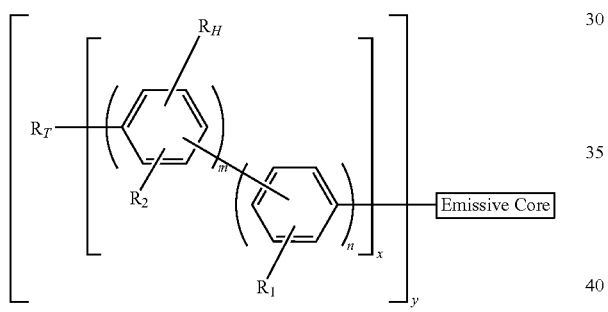

wherein the emissive core comprises a metal atom and a plurality of ligands coordinated to the metal atom, and wherein each branch is linked to one of the plurality of ligands. The emissive core represents the portion of the compound molecule that, if it were to be a separate and distinct molecular species, would serve as a dopant material in an emissive layer of an OLED. The metal may be any of various metals suitable for use in emissive dopants, including transition metals such as iridium, platinum, rhodium, osmium, ruthenium, rhenium, scandium, chromium, manganese, iron, cobalt, nickel, or copper. In some cases, iridium may be preferred because it is used in some of the most efficient emissive materials. The ligands may be any of various ligands that are suitable for use in emissive dopants, including photoactive ligands and ancillary ligands. Each of the ligands may be the same or different from other ligands.

As used herein, the term "branch" refers to the poly-phenylene chain contained within the "y"-indexed bracket. Variable "y" has an integer value of 1 to "p", wherein "p" is the formal oxidation state of the metal atom. Each variable "x" independently has an integer value of at least 2. Each variable "n" independently has an integer value of 0 or greater. Each variable "m" independently has an integer value of 1 or greater. By "independently," it is meant that each "x" is independent across all instances of "y"; each "n" is independent across all instances of "x" and across all instances of "y"; and each "m" is independent across all instances of "x" and across all instances of "y."

Each $R_H$ represents a host moiety. Each host moiety $R_H$ is independent across all instances of "m", across all instances of "x," and across all instances of "y." As used herein, the term "host moiety" refers to a pendant group on the poly-phenylene chain which could serve as a host material in an emissive layer if it were to be a separate and distinct molecular species. Various host moieties are suitable for use in the present invention, including aryl groups having at least two rings or heteroaryl groups having at least two rings, such as carbazole, triphenylene, phenanthrene, phenanthroline, and derivatives thereof.

In some cases, each host moiety $R_H$ has two or more rings, and preferably, three or more rings. In some cases, each host moiety $R_H$ has three to six rings. In some cases, all of the host moieties in the organometallic compound are the same.

For example, carbazole-containing host moieties may be used because they have a high triplet energy and good hole transporting properties. Suitable carbazole-containing host moieties include the following Group X (and also derivatives thereof having alkyl group, heteroalkyl group, aryl group, or heteroaryl group substitutions at any position on any of the rings).

Group X:

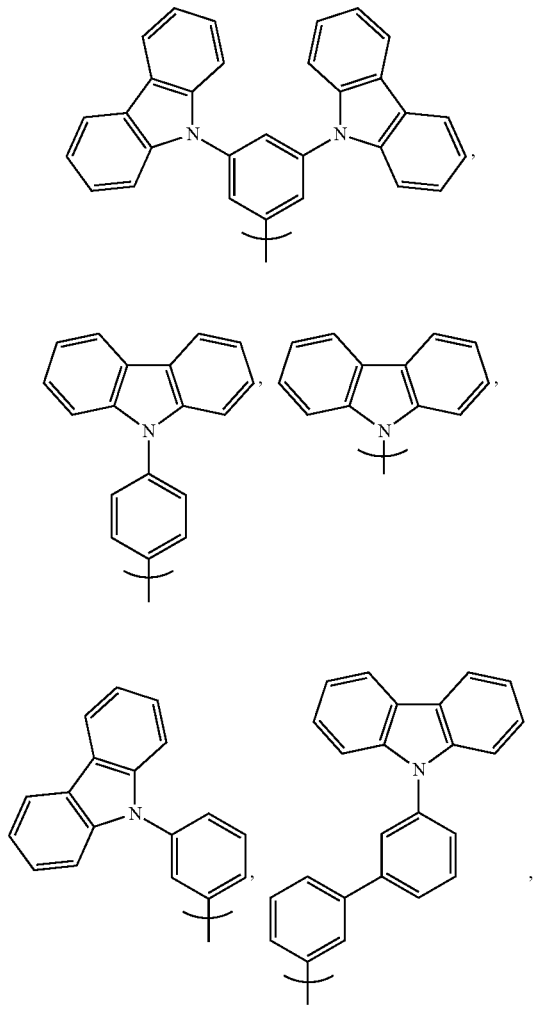

-continued
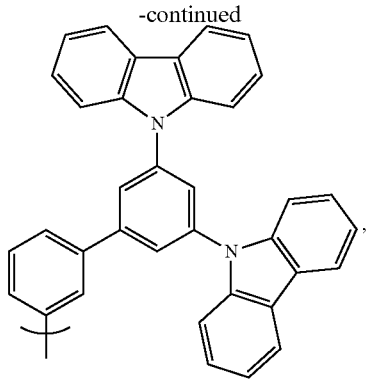
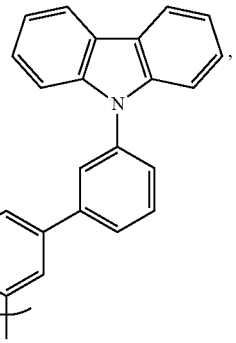
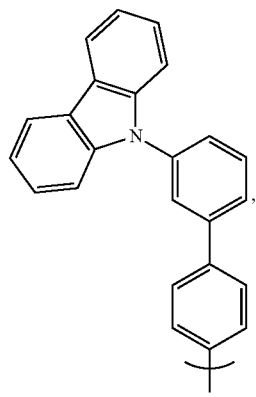
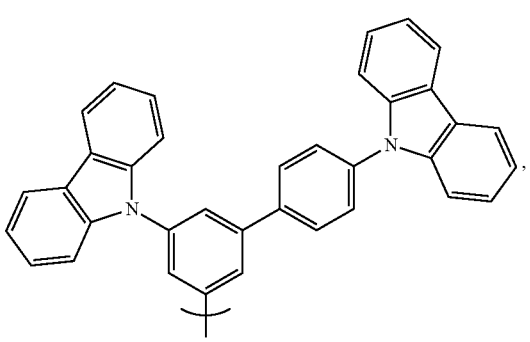
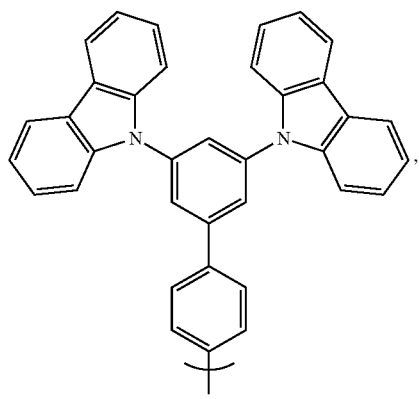
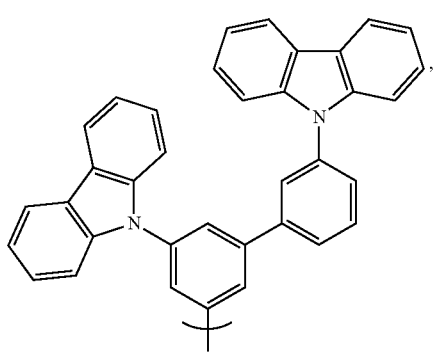
For example, suitable triphenylene-containing host moieties include the following Group Y (and also derivatives thereof having alkyl group, heteroalkyl group, aryl group, or heteroaryl group substitutions at any position on any of the rings):

Group Y:
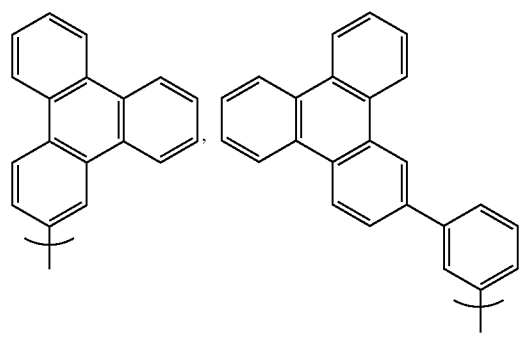
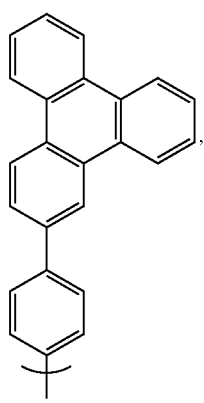
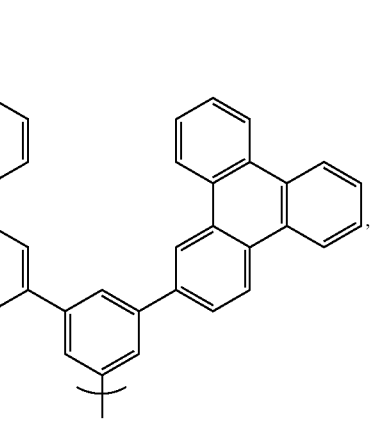
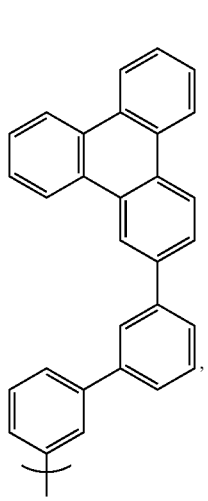
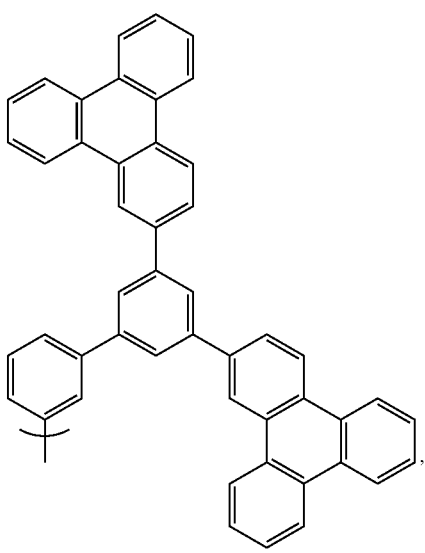
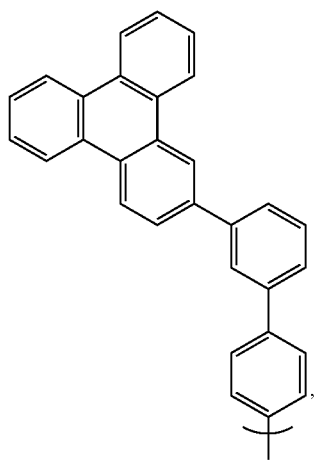
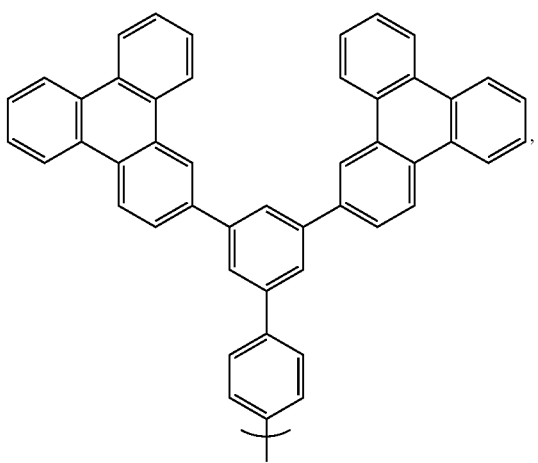

-continued
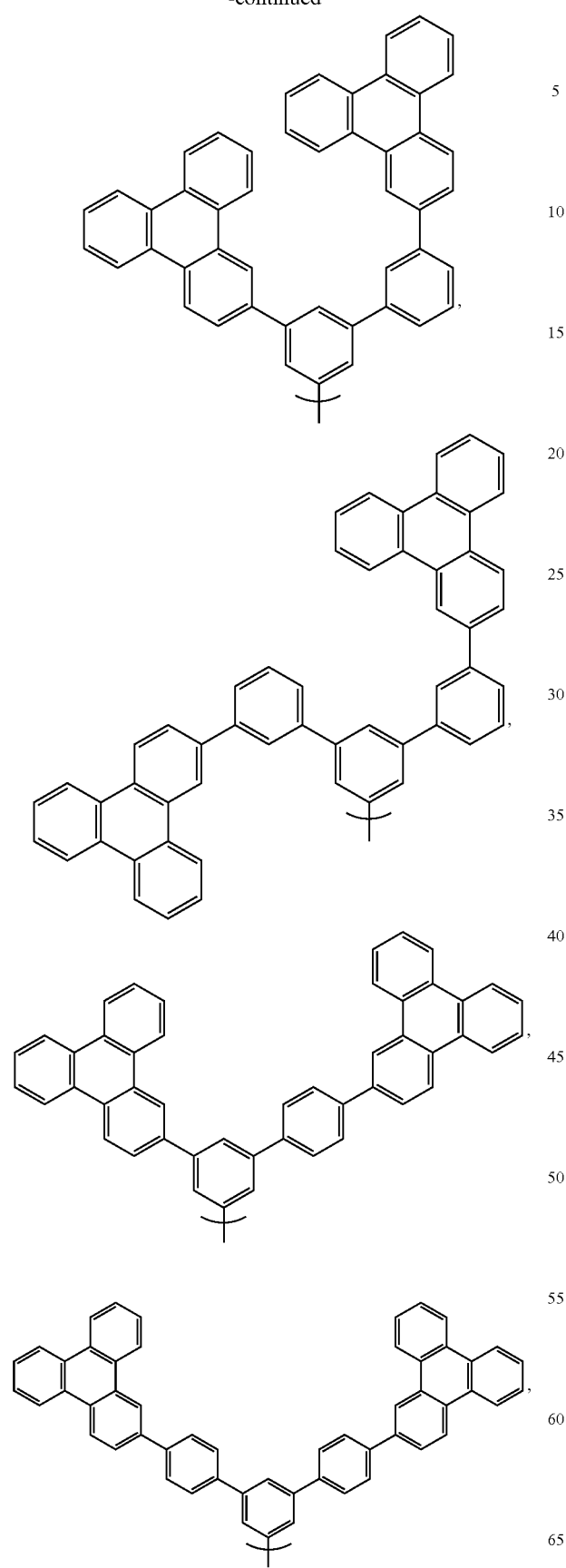
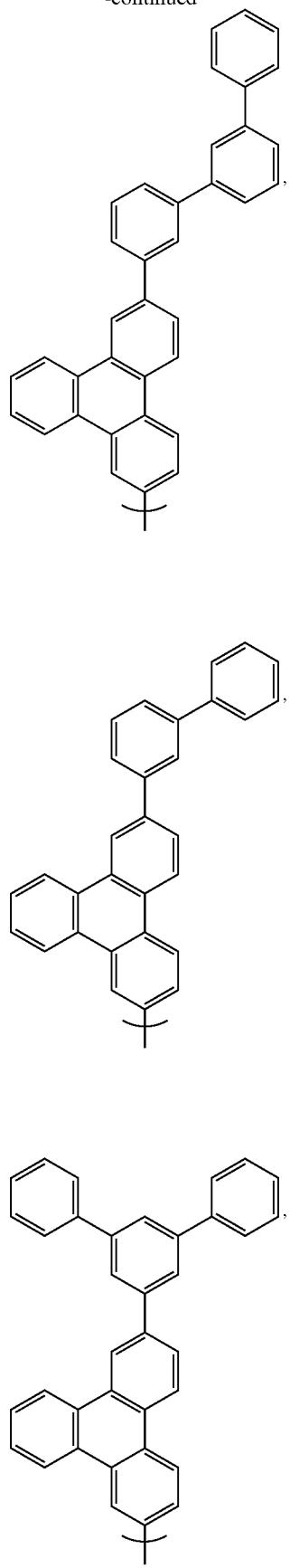

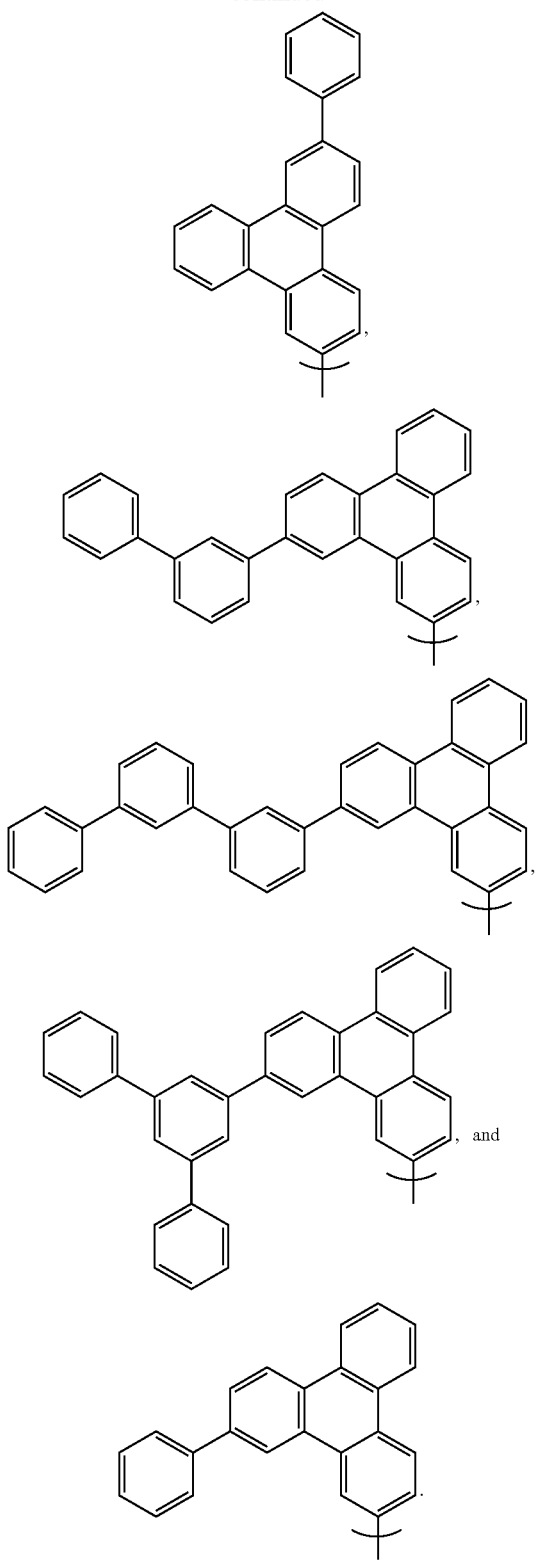
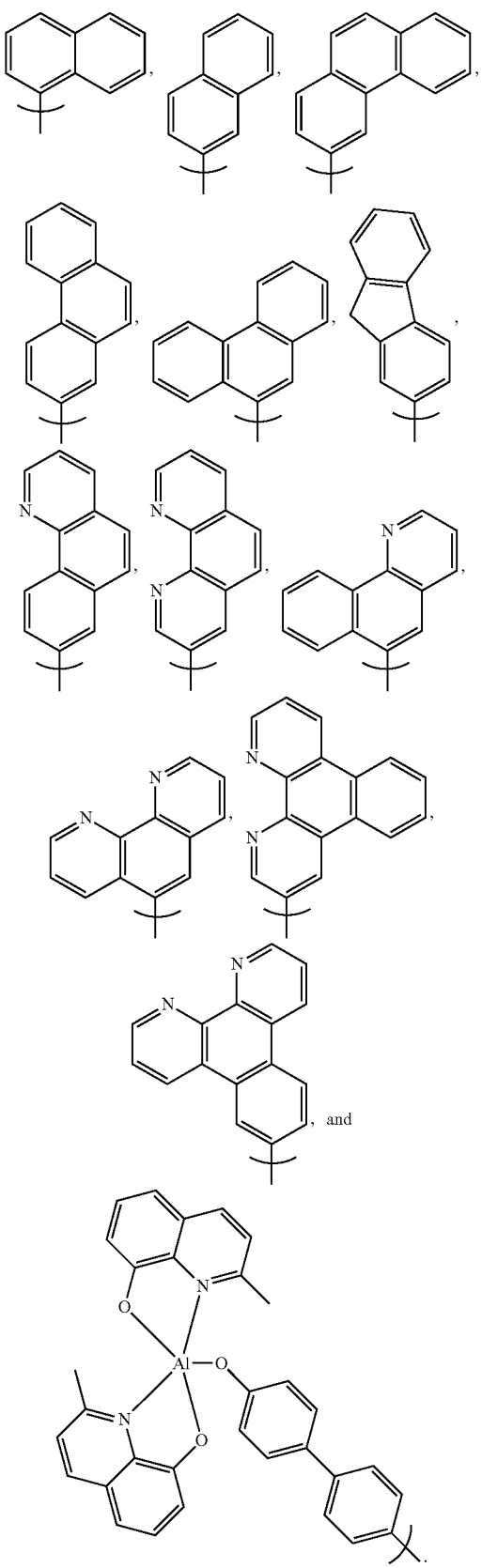
Other suitable host moieties include the following Group Z (and also derivatives thereof having alkyl group, heteroalkyl group, aryl group, or heteroaryl group substitutions at any position on any of the rings):

The quantity and the types of host moieties on the organometallic compound may be varied to tune the molecular weight ratio of the host moieties relative to the emissive core. Without intending to be bound by theory, the inventors believe that the stability and/or performance of an OLED using a blended host-dopant system in the emissive layer is sensitive to the concentration of the dopant. A dopant concentration that is too high or too low can reduce the stability and/or performance of the OLED. As such, in some cases, the molecular weight of the emissive core is from 0 to 30% of the sum of the molecular weights of all the branches with host moieties $R_H$. In some cases, the molecular weight of the emissive core is from 15% to 100% of the sum of the molecular weights of all the branches with host moieties $R_H$. In some cases, the molecular weight of the emissive core is from 15% to 30% of the sum of the molecular weights of all the branches with host moieties $R_H$. In some cases, the sum of the molecular weights of all the branches with host moieties $R_H$ is 3,400 amu or less. In some cases, the sum of the molecular weights of all the branches with host moieties $R_H$ is 1,600 amu or greater. In some cases, the sum of the molecular weights of all the branches with host moieties $R_H$ is from 1,600 to 3,400 amu.

In some cases, the quantity of host moieties may be varied by selecting the length of the branches. As such, in some cases, each variable "x" is independently in the range of 2 to 7. In some cases, the poly-phenylene chain in each branch contains 4 to 14 phenyl units. In some cases, additional host materials, that are separate and distinct from the organometallic compound, may be used in combination with the organometallic compound to further dilute the concentration of the emissive core.

Terminal groups $R_T$ serve to improve the solubility of the compound. As such, each terminal group $R_T$ may independently be an alkyl group, a heteroalkyl group, an aryl group, or a heteroaryl group. In some cases, a terminal group $R_T$ may be a host moiety.

Each of $R_1$ and $R_2$ represents one or more independently selected substitutions located on any position of their respective rings, wherein each of the substitutions are independently selected from the group consisting of: an alkyl group, a heteroalkyl group, an aryl group, and a heteroaryl group. Each $R_1$ is independent across all instances of "n", across all instances of "x," and across all instances of "y." Each $R_2$ is independent across all instances of "m", across all instances of "x," and across all instances of "y."

Each branch comprises a poly-phenylene chain with the host moieties as pendant groups on the poly-phenylene chain. When host moieties are pendant on a conjugated polymer chain, the host moieties have relatively low triplet energy levels because the electron energy levels are stabilized by the delocalized π-bonding along the chain. But to have efficient electro-phosphorescence, the triplet energy level of the host moiety should be higher than the phosphorescent dopant (i.e., the emissive core). Thus, in order to maintain the branches with the host moieties at high triplet energy levels, the organometallic compound may be designed such that π-conjugation in the poly-phenylene chain is limited or absent. This would inhibit quenching of emission from the emissive core. One way in which π-conjugation can be limited is by linking each phenyl unit in meta configuration with the adjacent phenyl units.

Many phosphorescent emissive layers, especially those made by vacuum thermal evaporation, are formed using separate host and dopant materials. These materials are often not very soluble and often have differing solubilities, presenting a problem if these layers are to be deposited by solution processing techniques (e.g., spin-coating or inkjet printing). As the solvent evaporates, one material may precipitate before another, resulting in non-uniform mixing and/or phase separation of the different materials or a film that is non-uniform. The organometallic compounds of the present invention combine the host and dopant functionalities in a single molecule. As such, in certain embodiments of the present invention, the problems of non-uniform mixing, phase separation, or crystallization during deposition is reduced.

In certain embodiments, the organometallic compound may be sufficiently soluble in an organic solvent (e.g., toluene or THF) to permit deposition of the organometallic compound by solution processing techniques, such as spin casting or ink jet printing. For example, the organometallic compound may have a solubility of at least 0.01 g in 10 ml of an organic solvent. The solubility of the organometallic compound may be adjusted in various ways, such as selecting the number and types of terminal groups $R_T$ and/or host moieties $R_H$; or selecting the length of each branch.

The length of each branch will vary depending upon the particular application. For example, each of the branches may be sufficiently long to provide the organometallic compound with solubility in an organic solvent; to inhibit crystallization or phase separation during deposition; and/or to provide uniform film formation. Also, branches that are too short may increase the relative concentration of the emissive core and allow excessive intermolecular quenching interactions. On the other hand, branches that are too long may dilute the emissive core, resulting in low efficiency when the organometallic compound is used in a device such as an OLED. In some cases, each variable "x" is independently in the range of 2 to 7. In some cases, the poly-phenylene chain in each branch contains 4 to 14 phenyl units.

In certain instances, the emissive core is represented by the formula:

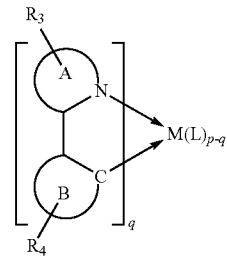

wherein M is the metal atom; wherein L is one or more of the plurality of ligands coordinated to M; wherein "p" is the formal oxidation state of the metal M; and wherein variable "q" has an integer value of 1 to "p". In some cases, ligand L may be acetylacetonate or a derivative of acetylacetonate. In some cases, one or more of the branches are linked to L, including cases where L is acetylacetonate or a derivative of acetylacetonate.

Structures A and B are each a 5 or 6-membered aromatic ring, wherein A-B represents a bonded pair of aromatic rings coordinated to M via a nitrogen atom on ring A and an sp² hybridized carbon atom on ring B. Each of rings A and B are optionally substituted with groups $R_3$ and $R_4$, respectively, wherein each of $R_3$ and $R_4$ represents one or more independently selected substitutions located on any position of their respective rings. Each of the substitutions are fused or linked to their respective rings, and each of the substitutions are independently selected from the group consisting of: an alkyl group, a heteroalkyl group, an aryl group, and a heteroaryl group. One or more of the branches are linked to ring A, ring B, or both. In some cases, one or more of the branches are linked to L. In some cases, ring A may be a quinoline or isoquinoline. In some cases, ring B may be phenyl. In some cases, the structure of A-B is:

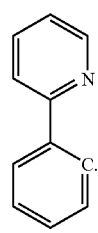

Lo, Shih-Chun et al., "The synthesis and properties of iridium cored dendrimers with carbazole dendrons," *Organic Electronics* 7:85-98 (2006) reports on dendrimers in which the dendrons contain carbazole units. As characteristic of dendrimers in general, the dendrimers described in Lo have a repeated branching structure.

Unlike dendrimers, the organometallic compounds disclosed herein do not have a repeated branching structure. As such, certain organometallic compounds disclosed herein may have one or more advantages over dendrimers that combine host and dopant functionalities. Because dendrimers have a repeated branching structure, functional groups (e.g., carbazoles) on the dendron branches will increase non-linearly (e.g. exponentially) with the addition of each successive generation. This makes it difficult to control the number of functional groups on the dendrimer. The organometallic compounds disclosed herein have host moieties as pendant groups on a poly-phenylene chain. As such, certain organometallic compounds disclosed herein provide a structure in which the number of host moieties can be varied linearly (e.g., sequentially, one at a time), allowing precise control over the number of host moieties on the compound.

Also, in dendrimers, the increasing complexity of the molecule with each successive generation of dendrons presents a challenge in synthesis. In order to "grow" another generation, an exponentially increasing number of functional groups have to be reacted. Because some of the functional groups often fail to react, the resulting dendrimers can have structural defects, or side products can be created, which can be difficult to remove.

The organometallic compounds disclosed herein have host moieties as pendant groups on a poly-phenylene chain. As such, certain organometallic compounds disclosed herein provide a structure that allows for the modular interchangeability of host moieties. This allows greater flexibility in tuning the molecule for the desired electrochemical or electroluminescent properties.

Also, in dendrimers, the steric interference created by the dendron branches can electronically isolate the emissive core, reducing device efficiency by inhibiting charge trapping by the emissive core and/or intermolecular charge transport. In certain organometallic compounds disclosed herein, the branches may sufficiently protect the emissive core from intermolecular quenching interactions, but without steric overcrowding around the emissive core.

Also, in dendrimers, the repeated branching structure requires the presence of an additional substitution at each branch point. This can affect the electrical properties of any functional group that serves as a branch point. In the organometallic compounds disclosed herein, there is no branching at the host moieties. As such, in certain organometallic compounds disclosed herein, the electrical properties of the host moieties are preserved.

Li, Yanqin et al., "Multifunctional platinum porphyrin dendrimers as emitters in undoped phosphorescent based light emitting devices," *Applied Physics Letters* 89:061125 (2006) reports on platinum porphyrin-based phosphorescent multifunctional first generation dendrimers incorporating a platinum porphyrin core as the emissive center and carbazole side groups as the hole, as well as energy transport fragments. The carbazole side groups are linked to the porphyrin core via ether linkages (C—O—C). In the organometallic compounds disclosed herein, only C—C linkages are used in the poly-phenylene chain. Without intending to be bound by theory, the inventors believe that C—C linkages (especially in aryl carbon to aryl carbon linkages, which are stronger than carbon to heteroatom linkages) can improve the electrochemical and electroluminescent stability of the compound in comparison to those with ether linkages.

EXPERIMENTAL

Specific representative embodiments of the invention will now be described, including how such embodiments may be made. It is understood that the specific methods, materials, conditions, process parameters, apparatus and the like do not necessarily limit the scope of the invention.

Compound Synthesis Examples

Figure 9:
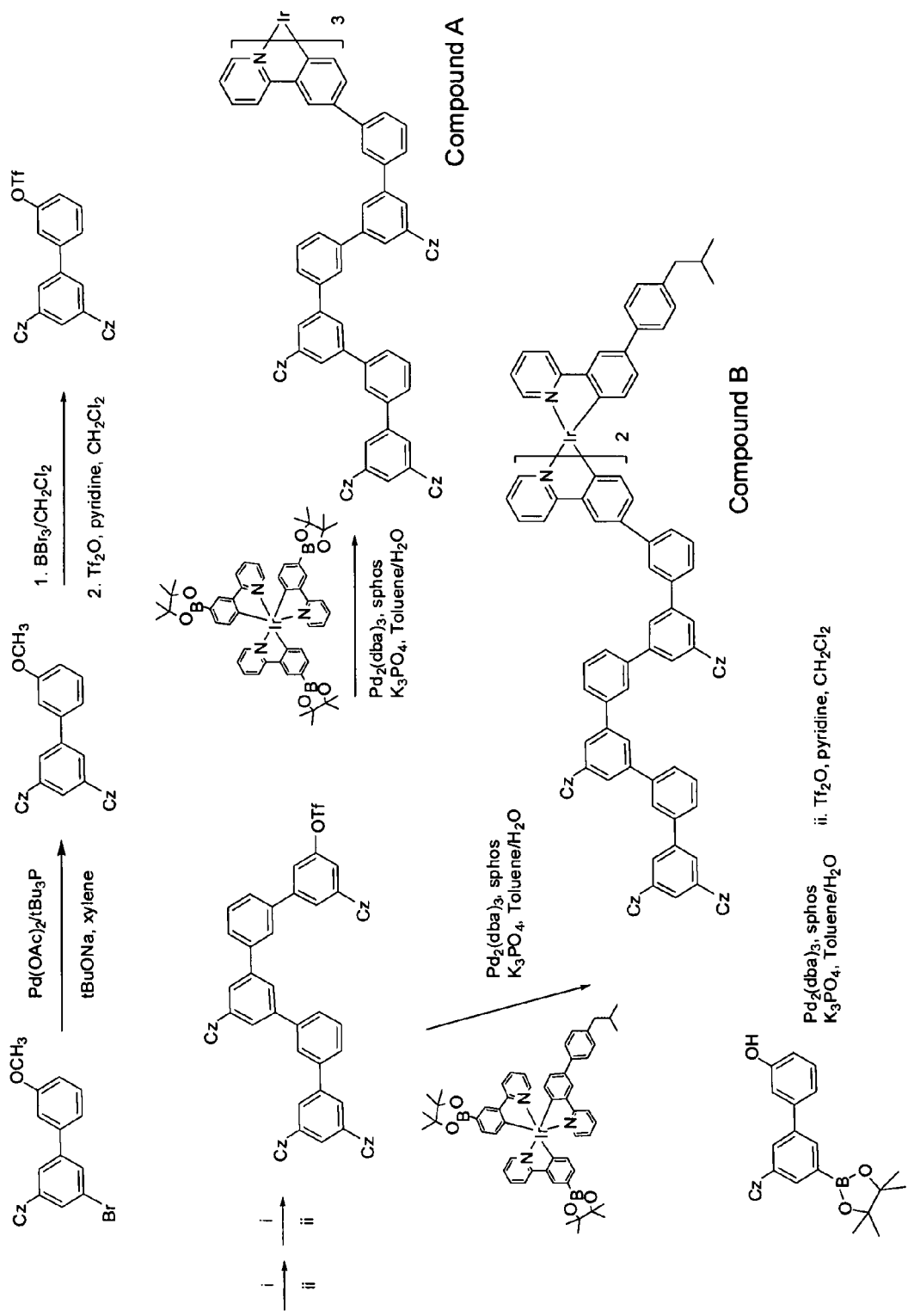
FIG. 9 shows the synthesis of Compounds A and B.
Figure 10:
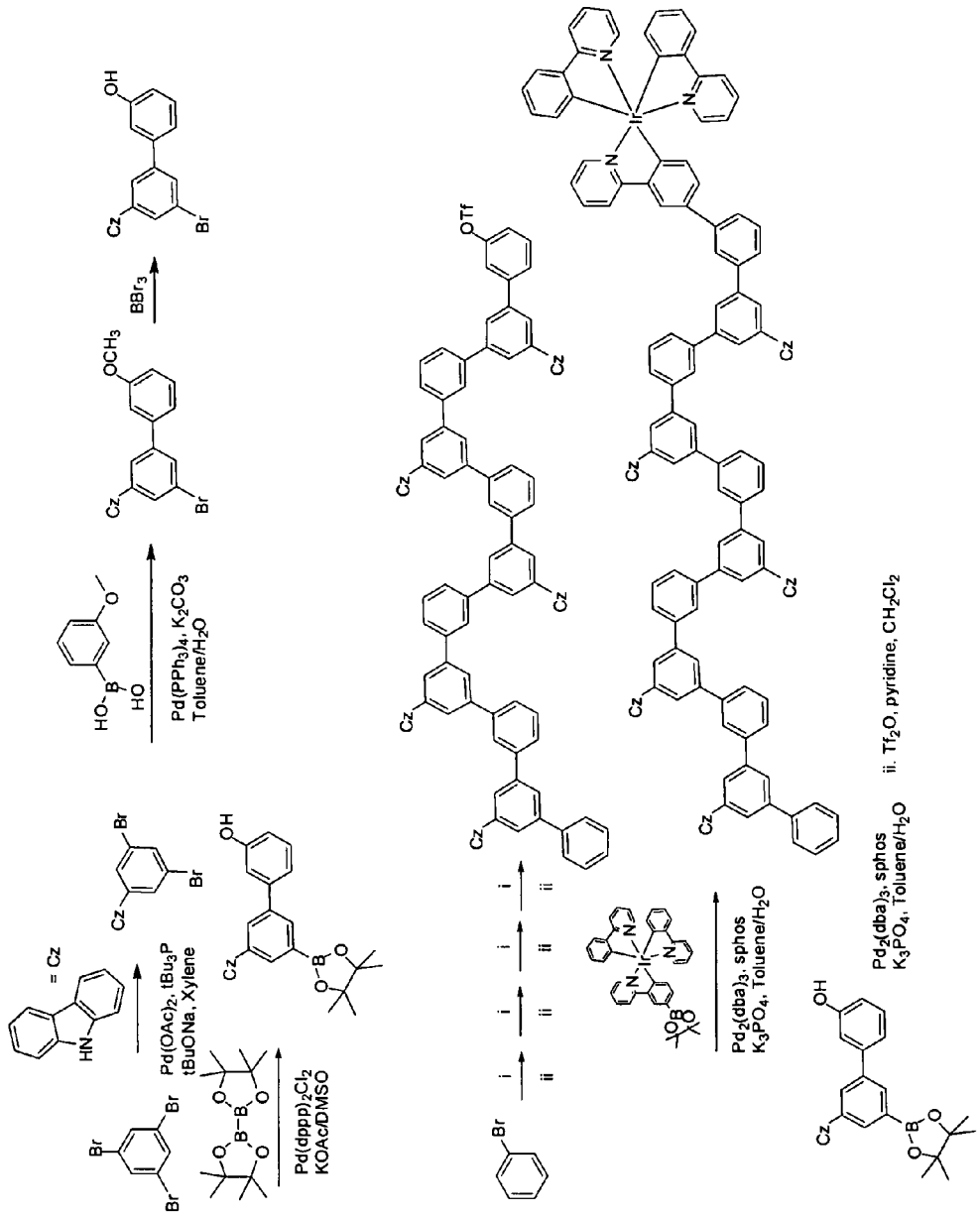
FIG. 10 shows the synthesis of Compound C.
Figure 11:
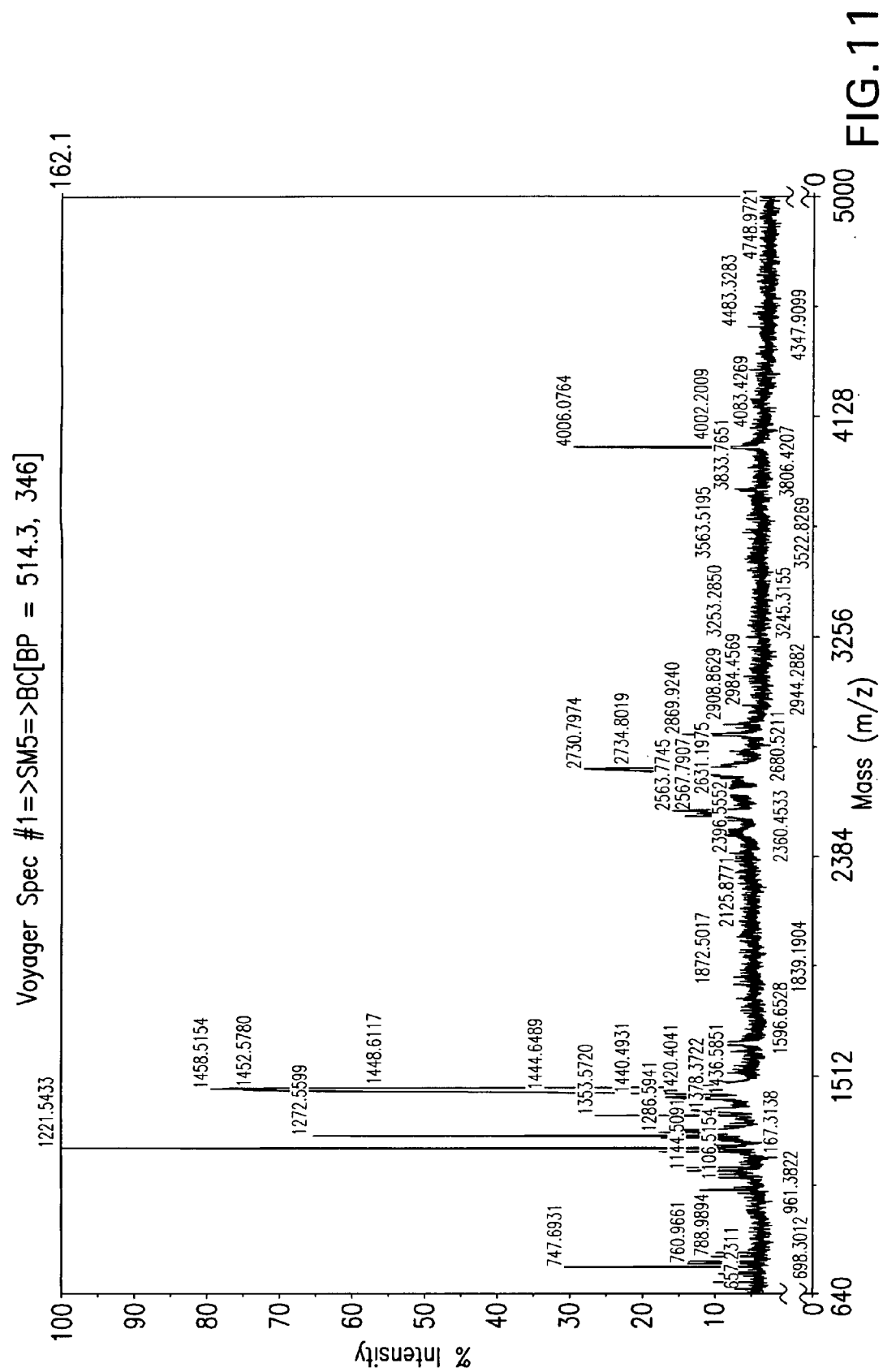
FIG. 11 shows the MALDI-TOF mass spectra for Compound A.

Compounds A, B, and C (shown below) were synthesized. FIG. 9 shows the synthesis of Compounds A and B. FIG. 10 shows the synthesis of Compound C.

Compound A

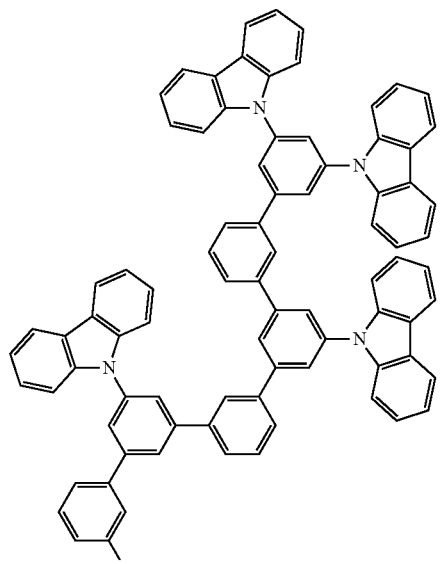

-continued
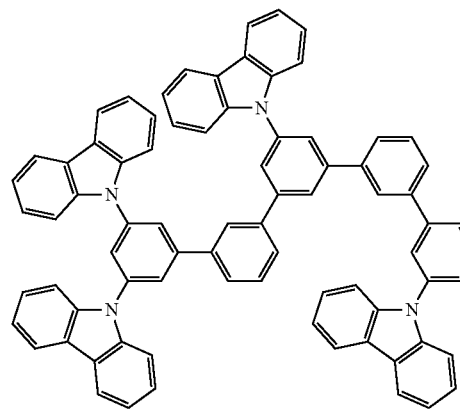
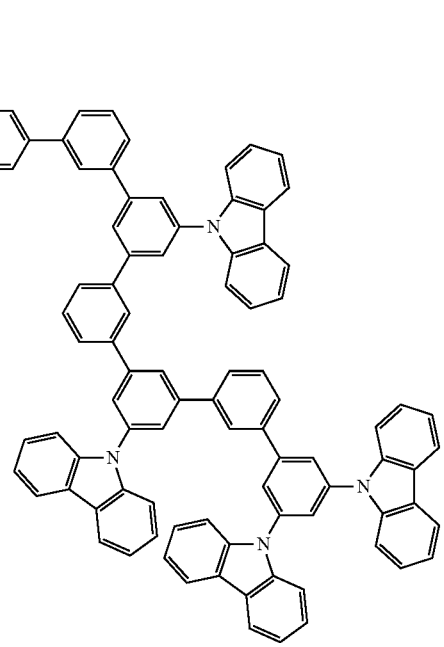
Compound B
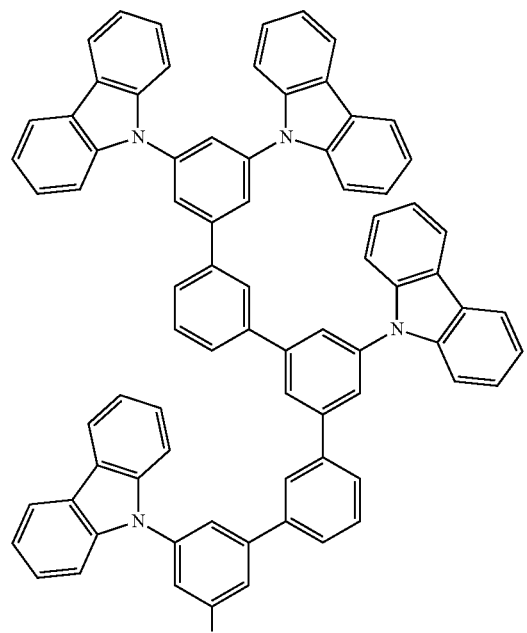

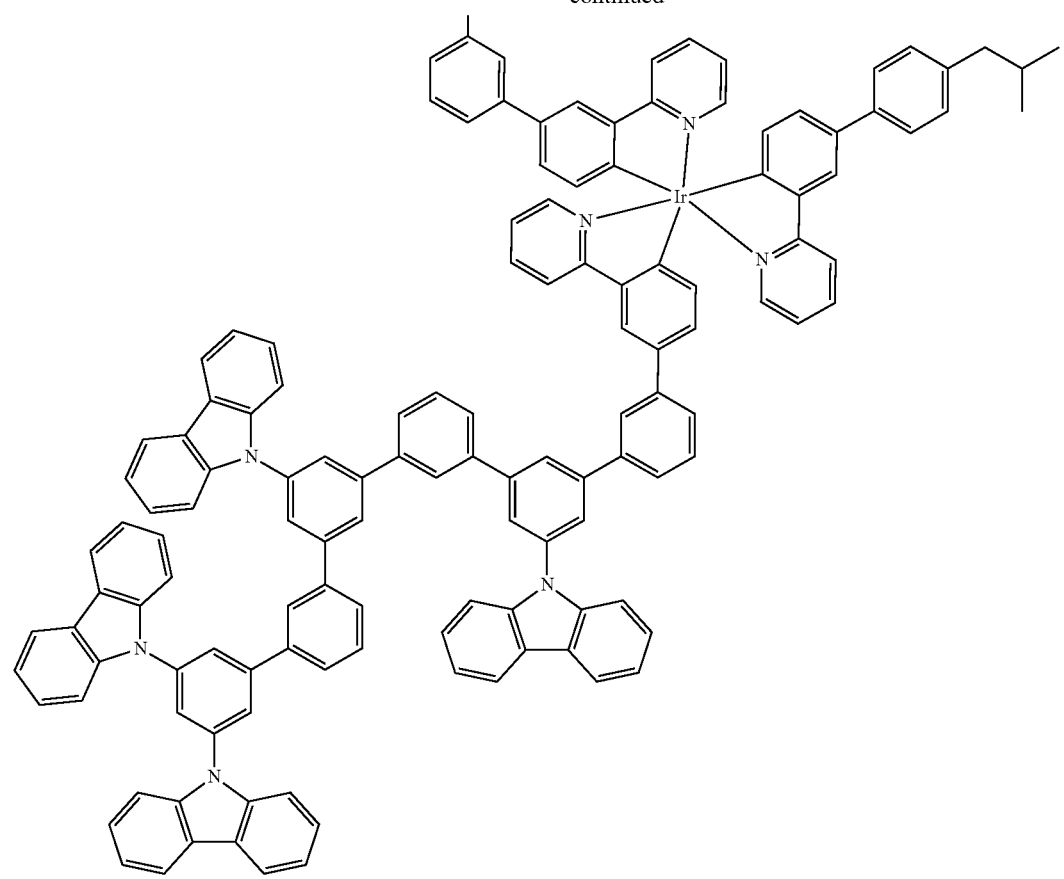
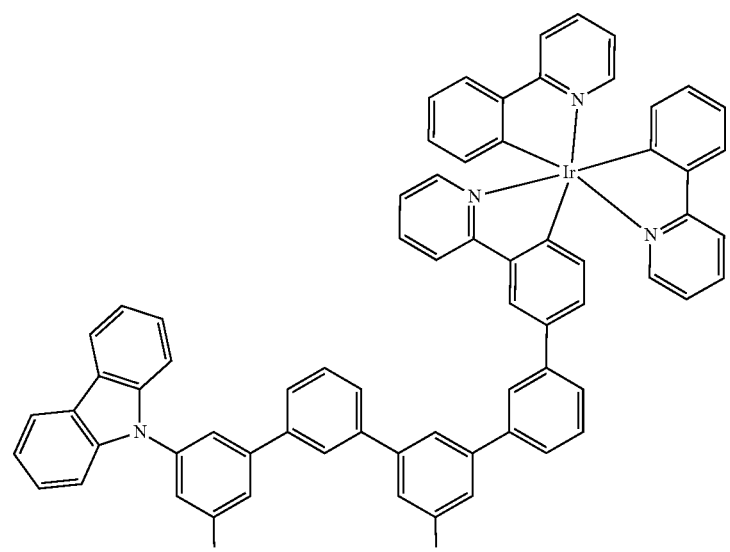
Compound C

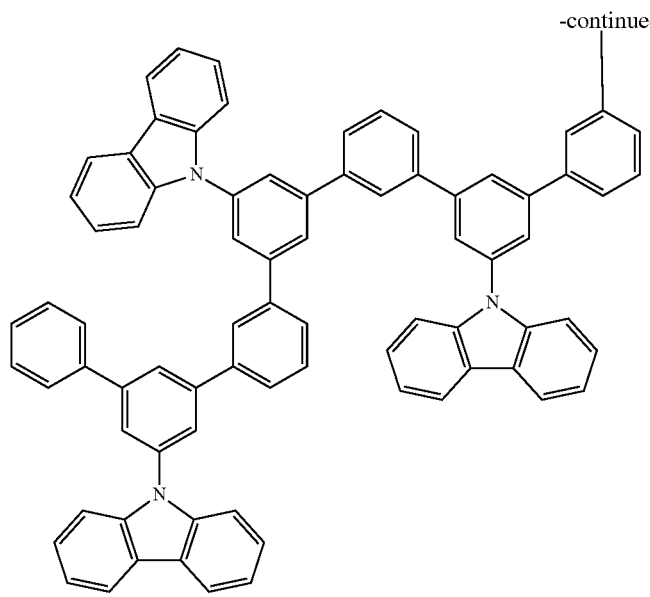
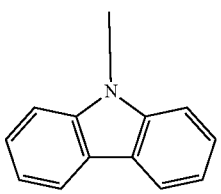

Device Examples

Examples Devices 1-12 were fabricated using compounds of the present invention. These devices were fabricated by spin-coating in nitrogen and high vacuum ($<10^{-7}$ Torr) thermal evaporation. The anode electrode was ~1200 Å of indium tin oxide (ITO) and the cathode was 10 Å of LiF followed by 1,000 Å of Al. All devices were encapsulated with a glass lid sealed with an epoxy resin in a nitrogen glove box (<1 ppm of $H_2O$ and $O_2$) immediately after fabrication, and with a moisture getter incorporated inside the package.

In Device Example 1, the hole injection layer was formed by spin-coating a cyclohexane solution of Compound 1 (0.5 wt %) at 4000 rpm followed by thermal cross-linking at 250° C. for 30 minutes. The resulting film thickness was about 130 Å. The hole transporting layer was formed by spin-coating a toluene solution of Compound 2 (1.0 wt %) at 4000 rpm followed by thermal cross-linking at 200° C. for 30 minutes. The resulting film thickness was about 250 Å. The emissive layer (EML) was formed by spin-coating a toluene solution of Compound A (1.0 wt %) at 4000 rpm followed by heating at 100° C. for 60 minutes. The resulting film thickness was about 320 Å. A 50 Å layer of 2,3,6,7,10,11-hexaphenyltriphenylene (HPT) was deposited by vacuum thermal evaporation as an electron transport layer 2 (ETL2) and a 500 Å layer of $Alq_3$ was deposited by vacuum thermal evaporation as an electron transport layer 2 (ETL1).

Device Example 2 had the same architecture as Device Example 1 except that the EML was spin-coated at 2000 rpm and the resulting film thickness was about 420 Å. Device Example 3 had the same architecture as Device Example 1 except that the ETL2 was 100 Å of BAlq. Device Example 4 had the same architecture as Device Example 2 except that the ETL2 was 100 Å of BAlq. Device Example 5 had the same architecture as Device Example 2 except that the EML was formed by spin-coating a 0.5 wt % solution and the ETL2 was 100 Å of Compound 3. Device Example 6 had the same architecture as Device Example 5 except that the EML was spin-coated at 4000 rpm. Device Example 7 had the same architecture as Device Example 1 except that the EML was spin-coated from a toluene solution of Compound B (0.5%) at 2000 rpm.

Device Example 8 had the same architecture as Device Example 7 except that the EML was spin-coated at 4000 rpm. Device Example 9 had the same architecture as Device Example 7 except that the ETL2 was 100 Å of Compound 3. Device Example 10 had the same architecture as Device Example 8 except that the ETL2 was 100 Å of Compound 3.

Device Example 11 had the same architecture as Device Example 2 except that the HIL was spin-coated from a 0.25 wt % cyclohexane solution of Compound 1 and a conductivity dopant CD1 (5 wt % of Compound 1); the HTL was spin-coated at 2000 rpm and the EML was spin-coated from a toluene solution of Compound C (0.75%). Device Example 12 had the same architecture as Device Example 11 except that the EML solution contained 0.375 wt % of Compound C and 0.375 wt % of Compound 4 as an additional host material.

Compound 1

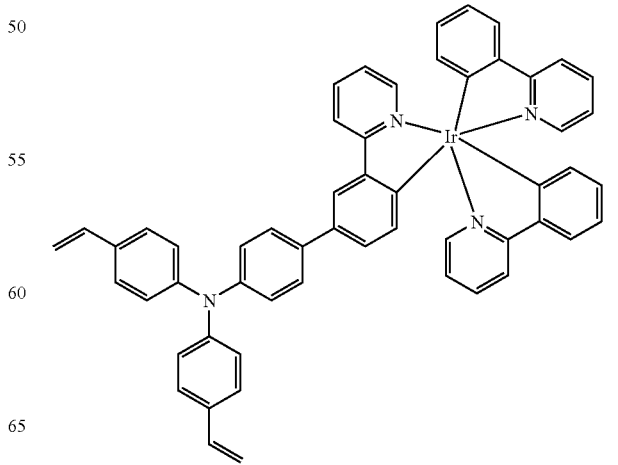

Compound 2

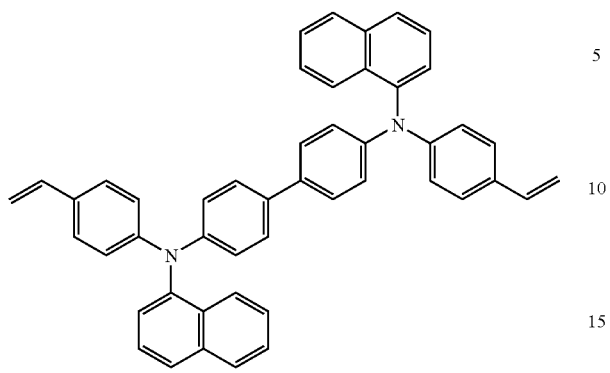

Compound 3

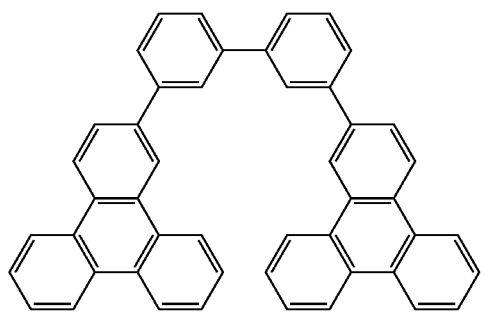

Compound 4

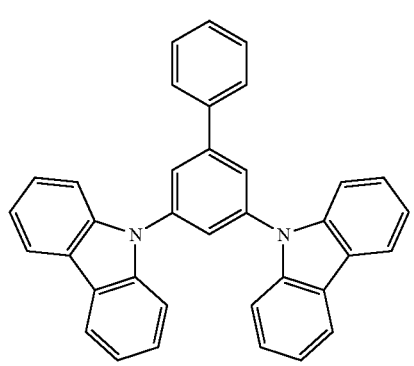

Compound CD1

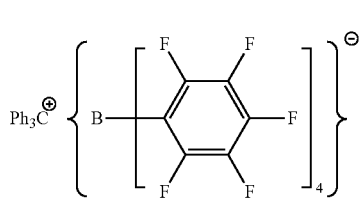

HPT

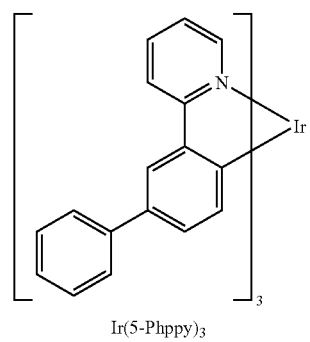

A comparative example device was made completely by vacuum thermal evaporation. The organic stack was as follows: from the ITO surface, 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å CBP doped with 4.5 wt % of Ir(5-Phppy)$_3$ as the emissive layer (EML), 100 Å of BAlq as the ETL2, and 400 Å of tris(8-hydroxyquinolinato)aluminum (Alq$_3$) as the ETL1.

Ir(5-Phppy)$_3$

A summary of the device characteristics and fabrication are shown in Tables 1a-1d below. Table 1d also includes the luminous efficiency at 1000 cd/m$^2$, the lifetime (T$_{0.8}$, defined as the time required for the luminance to decay to 80% of its initial value under constant DC current), and CIE coordinates (at J=10 mA/cm$^2$). The current-voltage-luminance (IVL) characteristics of the devices are shown in FIGS. 3-8.

TABLE 1a

| | | HIL | | | |
|---|---|---|---|---|---|
| Device Example | Compound | spin rate (×1000 rpm) | solution conc (wt %) | thickness (Å) | HIL Dopant |
| 1 | 1 | 4 | 0.5 | 130 | none |
| 2 | 1 | 4 | 0.5 | 130 | none |
| 3 | 1 | 4 | 0.5 | 130 | none |
| 4 | 1 | 4 | 0.5 | 130 | none |
| 5 | 1 | 4 | 0.5 | 130 | none |
| 6 | 1 | 4 | 0.5 | 130 | none |
| 7 | 1 | 4 | 0.5 | 130 | none |
| 8 | 1 | 4 | 0.5 | 130 | none |
| 9 | 1 | 4 | 0.5 | 130 | none |

TABLE 1a-continued

| | | HIL | | | |
|---|---|---|---|---|---|
| Device Example | Compound | spin rate (×1000 rpm) | solution conc (wt %) | thickness (Å) | HIL Dopant |
| 10 | 1 | 4 | 0.5 | 130 | none |
| 11 | 1 | 4 | 0.25 | 100 | CD1 |
| 12 | 1 | 4 | 0.25 | 100 | CD1 |
| Comparative Example 1 | | | CuPc | | |

TABLE 1b

| | | HTL | | |
|---|---|---|---|---|
| Device Example | Compound | spin rate (×1000 rpm) | solution conc (wt %) | thickness (Å) |
| 1 | 2 | 4 | 1 | 250 |
| 2 | 2 | 4 | 1 | 250 |
| 3 | 2 | 4 | 1 | 250 |
| 4 | 2 | 4 | 1 | 250 |
| 5 | 2 | 4 | 1 | 250 |
| 6 | 2 | 4 | 1 | 250 |
| 7 | 2 | 4 | 1 | 250 |
| 8 | 2 | 4 | 1 | 250 |
| 9 | 2 | 4 | 1 | 250 |
| 10 | 2 | 4 | 1 | 250 |
| 11 | 2 | 2 | 1 | 350 |
| 12 | 2 | 2 | 1 | 350 |
| Comparative Example 1 | | | NPD | | |

TABLE 1c

| | | | EML | | |
|---|---|---|---|---|---|
| Device Example | Emitter | Additional Host | spin rate (×1000 rpm) | solution conc (wt %) | thickness (Å) |
| 1 | A | none | 4 | 1 | 320 |
| 2 | A | none | 2 | 1 | 420 |
| 3 | A | none | 4 | 1 | 320 |
| 4 | A | none | 2 | 1 | 420 |
| 5 | A | none | 2 | 0.5 | 270 |
| 6 | A | none | 4 | 0.5 | 220 |
| 7 | B | none | 2 | 0.5 | 270 |
| 8 | B | none | 4 | 0.5 | 220 |
| 9 | B | none | 2 | 0.5 | 270 |
| 10 | B | none | 4 | 0.5 | 220 |
| 11 | C | none | 2 | 0.75 | 300 |
| 12 | C | 4 | 2 | 0.75 | 300 |
| Comparative Example 1 | | | CBP: Ir(5-Phppy)$_3$ | | |

TABLE 1d

| Device Example | ETL2 | LE at 1000 cd/m$^2$ (cd/A) | $T_{0.8}$ at $L_0$ = 2000 cd/m$^2$ (hr) | CIE |
|---|---|---|---|---|
| 1 | HPT | 33 | 1.9 | 0.32, 0.63 |
| 2 | HPT | 18 | 1.3 | 0.34, 0.62 |
| 3 | BAlq | 5.5 | NA | 0.35, 0.59 |
| 4 | BAlq | 5.3 | NA | 0.34, 0.60 |
| 5 | 3 | 31.2 | 1.5 | 0.34, 0.62 |
| 6 | 3 | 28.8 | 2 | 0.33, 0.62 |
| 7 | HPT | 22.9 | 2.2 | 0.36, 0.61 |
| 8 | HPT | 22.9 | 2.5 | 0.35, 0.61 |
| 9 | 3 | 21.3 | 8.2 | 0.36, 0.61 |
| 10 | 3 | 22.2 | 8.2 | 0.36, 0.61 |
| 11 | HPT | 24.8 | 3.8 | 0.34, 0.62 |
| 12 | HPT | 30.6 | 66 | 0.32, 0.63 |
| Comparative Example 1 | BAlq | 27 | 3400 | 0.31, 0.64 |

The CIE coordinate data show that the emission colors of the devices using Compounds A-C are nearly identical to that of the device of the comparative example. This indicates that the electronic and electroluminescent properties of the emissive core of Compounds A-C were not affected by linking of the host moieties. This may be due to the lack of π-conjugation through the meta linkages in the poly-phenylene chain.

The data in Table 1d also show that the luminous efficiencies for some of the example devices are the same as or exceed that of the comparative device. This indicates that linking of the host moieties to the emissive core does not interfere with the effective charge recombination or quench emission from the emissive core.

The inventors believe that Compound A may preferentially have hole transporting properties. This belief is based on the observation that Device Examples 3 and 4 have relatively low efficiency and slightly more red-shifted CIE coordinates. These two devices use the weak hole-blocking material BAlq in the ETL, which may allow hole leakage out of the emissive layer. In comparison, Device Examples 1, 2, and 5-11, which use stronger hole-blocking materials (HPT and compound 3) in the ETLs, are markedly more efficient. One possible explanation for this hole transporting property of Compound A is the fact that the emissive component (i.e., the emissive core) constitutes a relatively high weight percentage of the molecule—22 wt % based on the structure of Ir(5-Phppy)$_3$ as the emissive component, which is greater than that of an optimized VTE (vacuum thermal evaporation) device (typically 4-12 wt %). Accordingly, the inventors believe that certain compounds of the present invention (e.g., those in which the host moieties constitute a relatively large weight percentage ratio in comparison to the emissive core) have certain hole transporting characteristics, which may confer improved device performance.

In many molecules with combined host-dopant functionality, the host is a poor hole transporter relative to the dopant. In such molecules, increasing the amount of dopant functionality (i.e., decreasing the weight proportion of the molecule that constitutes the host), increases the hole conductivity of the emissive layer. Conversely, increasing the weight proportion of the molecule that constitutes the host will decrease the hole conductivity of the emissive layer. As such, the hole conductivity of the layer can be adjusted by varying the quantities and types of host moieties and/or the emissive cores on the organometallic compound, depending upon the particular device architecture. For example, in some cases, decreasing the hole conductivity of the emissive layer may be desirable in order to reduce charge build-up on the cathode side of the emissive layer, which would negatively impact device efficiency and stability.

Although Device Examples 1-11 have relatively short lifetimes, the inventors believe that longer lifetimes may be achieved without affecting device efficiency by diluting the emissive component of the compounds. This belief is based on the observation that Device Example 12, which uses an additional host material in the emissive layer, was the most stable of the example devices and one of the most efficient. As such, dilution of the emissive core may be achieved by adding another host material or by increasing the number of host moieties in the compound. Where the organometallic compounds are deposited by solution processing, the additional host material may also be deposited by solution processing.

In another aspect, the present invention provides an organic electronic device comprising an organometallic compound of the present invention. The organic electronic device comprises an anode, a cathode, and a first organic layer disposed between the anode and the cathode, wherein the organic layer comprises an organometallic compound of the present invention.

In certain instances, the first organic layer is an electroluminescent layer. In certain instances, the first organic layer may further comprise a host material that is separate and distinct from the organometallic compound. In certain instances, the first organic layer is formed by solution processing. The organic electronic device may be an organic light-emitting device, and as such, further comprise other organic layers, such a hole injection layer, a hole transport layer, or an electron transport layer.

In yet another aspect, the present invention provides a method for making an organic electronic device using an organometallic compound of the present invention. The method comprises providing a first electrode disposed on a substrate; forming a first organic layer over the first electrode, wherein the first organic layer comprises an organometallic compound of the present invention; and forming a second electrode disposed over the first organic layer.

In certain instances, the first organic layer is formed by depositing the organometallic compound by solution processing. The organic electronic device may further comprise other organic layers, such a hole injection layer, a hole transport layer, or an electron transport layer. One or more of these others layers, such as the hole injection or the hole transport layers, may be formed by solution processing.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting.

What is claimed is:

1. An organometallic compound comprising one or more branches linked to an emissive core as represented by the formula:

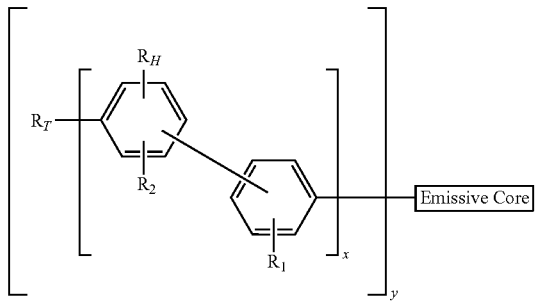

wherein the emissive core comprises a metal atom and a plurality of ligands coordinated to the metal atom;
wherein each branch is linked to one of the plurality of ligands;
wherein variable "y" has an integer value of 1 to 3;
wherein each variable "x" independently has an integer value of at least 2;
wherein each host moiety $R_H$ is independently an aryl group having at least two rings or a heteroaryl group having at least two rings;

wherein each $R_T$ is an optional terminal group independently selected from the group consisting of: an alkyl group, a heteroalkyl group, an aryl group, and a heteroaryl group;
wherein each of $R_1$ and $R_2$ represents one or more optional independently selected substitutions located on any position of their respective rings, wherein each of the substitutions are independently an alkyl group or a heteroalkyl group.

2. The organometallic compound of claim 1, wherein each phenyl unit within the chain is linked to the adjacent phenyl units in meta configuration.

3. The organometallic compound of claim 1, wherein the emissive core is represented by the formula:

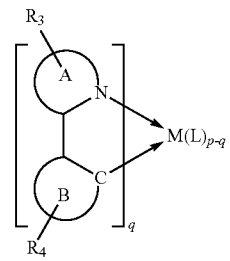

wherein M is the metal atom;
wherein L is one or more of the plurality of ligands coordinated to M;
wherein "p" is the formal oxidation state of the metal M;
wherein variable "q" has an integer value of 1 to "p";
wherein A and B are each a 5 or 6-membered aromatic ring, and wherein A-B represents a bonded pair of aromatic rings coordinated to M via a nitrogen atom on ring A and an $sp^2$ hybridized carbon atom on ring B;
wherein each of rings A and B are optionally substituted with groups $R_3$ and $R_4$, respectively, wherein each of $R_3$ and $R_4$ represents one or more independently selected substitutions located on any position of their respective rings, wherein each of the substitutions are fused or linked to their respective rings, and wherein each of the substitutions are independently selected from the group consisting of: an alkyl group, a heteroalkyl group, an aryl group, and a heteroaryl group;
wherein one or more of the branches are linked to ring A, ring B, or both.

4. The organometallic compound of claim 3, wherein the structure A-B is:

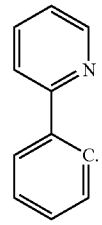

5. The organometallic compound of claim 3, wherein ring A is a quinoline or isoquinoline and ring B is a phenyl.

6. The organometallic compound of claim 5, wherein variable "q" is 2 and L is acetylacetonate or a derivative of acetylacetonate.

7. The organometallic compound of claim 6, wherein one of the branches is linked to L.

8. The organometallic compound of claim 1, wherein each $R_H$ independently has 3 to 6 rings.

9. The organometallic compound of claim 1, wherein each $R_H$ is independently selected from the group consisting of: carbazole, triphenylene, phenanthrene, phenanthroline, and derivatives thereof.

10. The organometallic compound of claim 1, wherein each variable "x" is independently in the range of 2 to 7.

11. The organometallic compound of claim 1, wherein the poly-phenylene chain in each branch contains 4 to 14 phenyl units.

12. The organometallic compound of claim 1, wherein the molecular weight of the emissive core is from 15% to 100% of the sum of the molecular weights of all the branches with host moieties $R_H$.

13. The organometallic compound of claim 1, wherein the molecular weight of the emissive core is from 0 to 30% of the sum of the molecular weights of all the branches with host moieties $R_H$.

14. The organometallic compound of claim 1, wherein the organometallic compound has a solubility of at least 0.01 g in 10 ml of an organic solvent.

15. The organometallic compound of claim 1, wherein the metal atom is iridium.

16. The organometallic compound of claim 1, wherein the host moieties $R_H$ are selected from Group X or derivatives thereof having alkyl group, heteroalkyl group, aryl group, or heteroaryl group substitutions at any position on any of the rings in the host moieties, wherein Group X consists of:

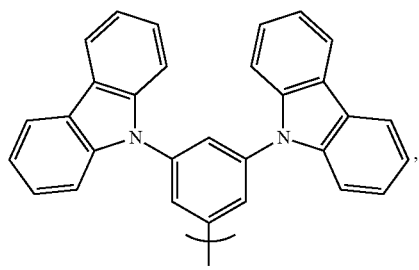

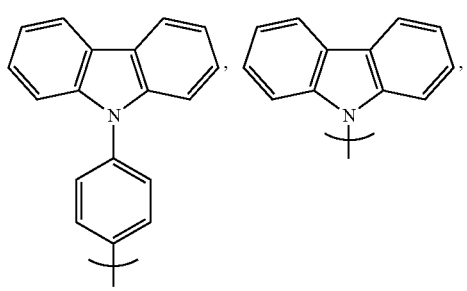

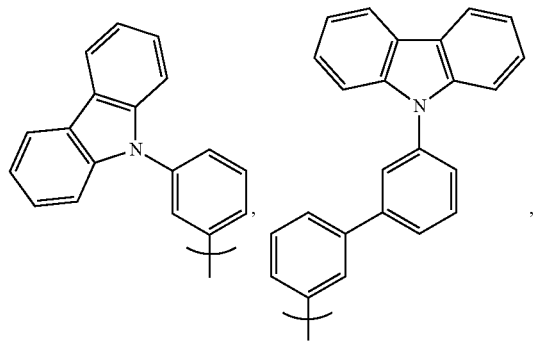

-continued

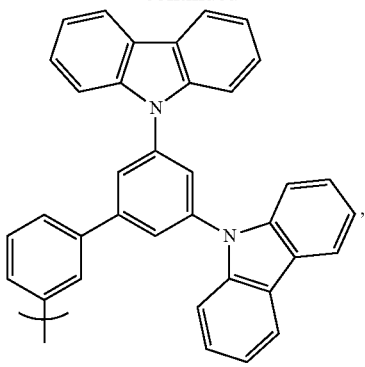

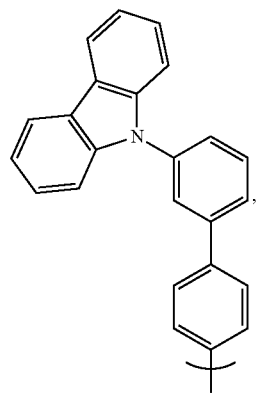

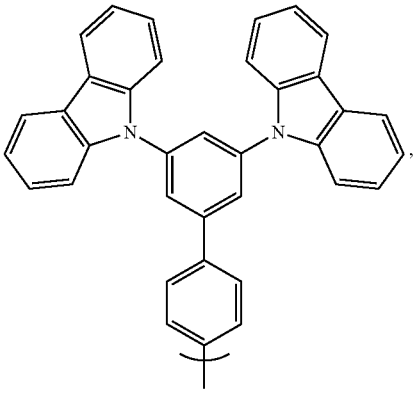

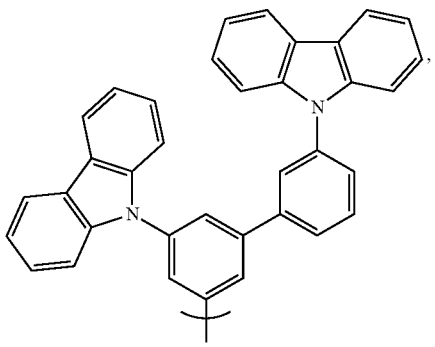

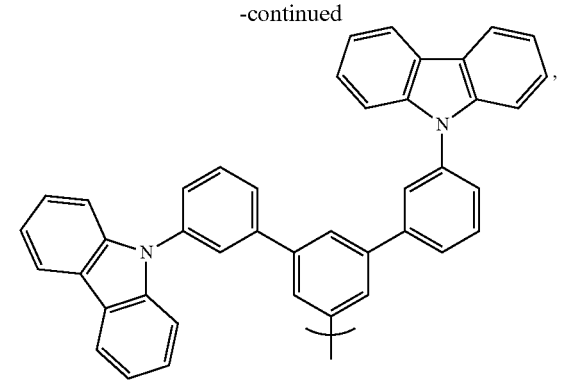
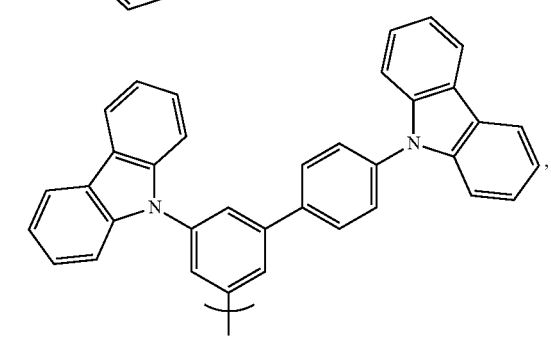
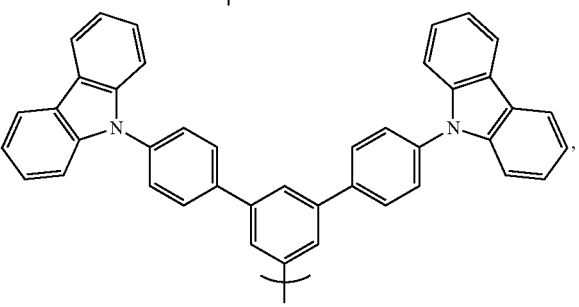
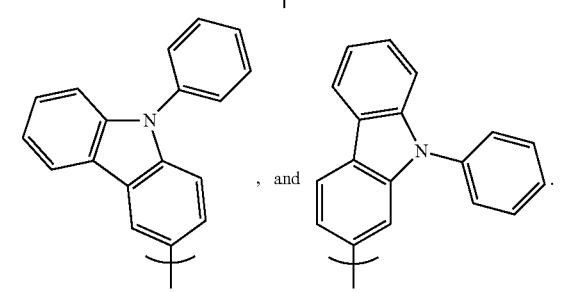
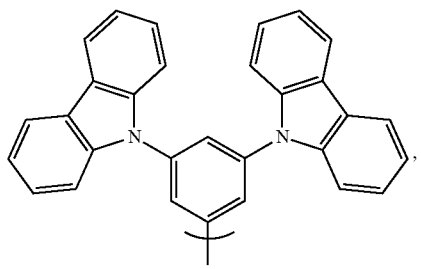
17. The organometallic compound of claim 1, wherein the host moieties $R_H$ are selected from Group X, Group Y, Group Z, or derivatives thereof having alkyl group, heteroalkyl group, aryl group, or heteroaryl group substitutions at any position on any of the rings in the host moieties,
wherein Group X consists of:
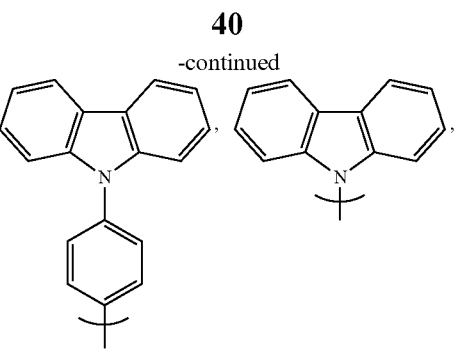
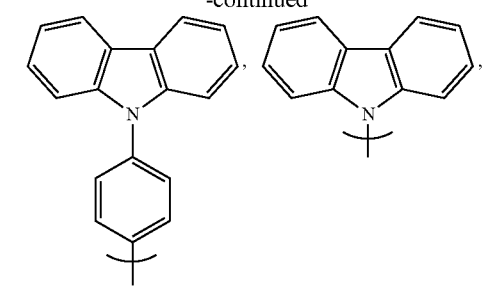
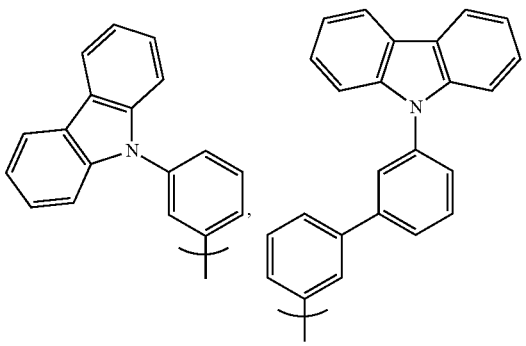
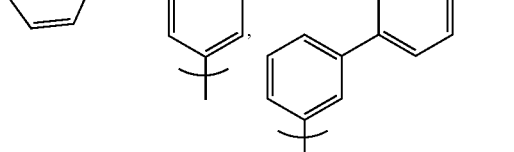
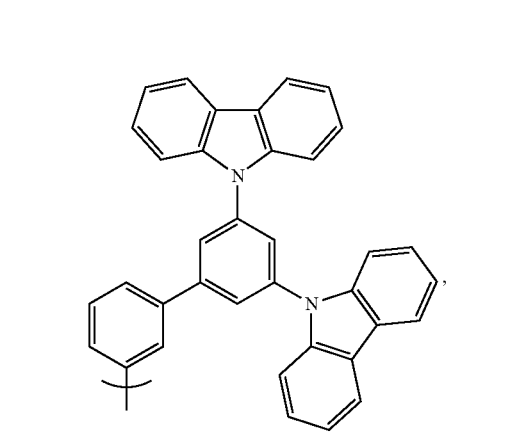
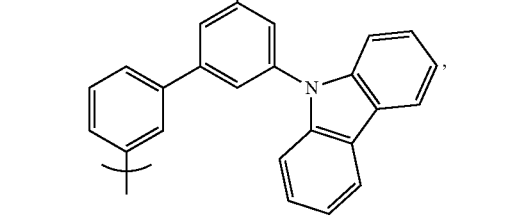

-continued
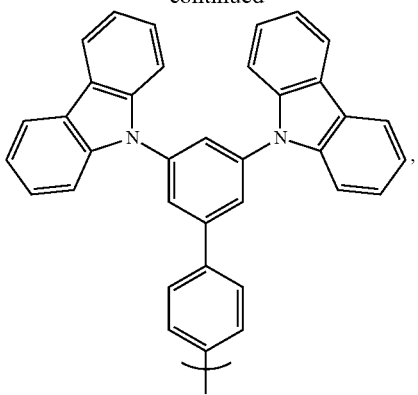
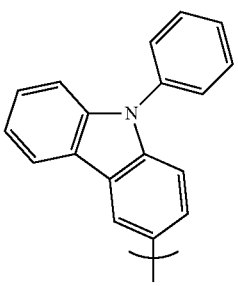, and 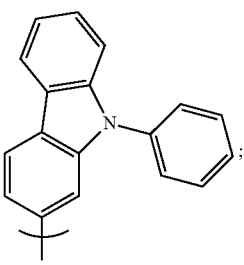;
wherein Group Y consists of:
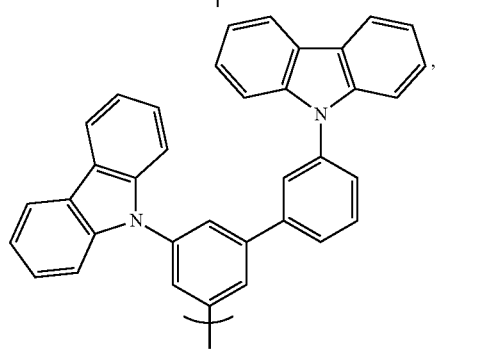
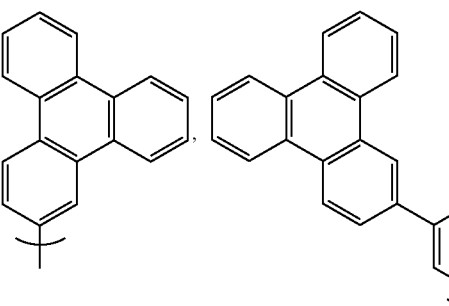,
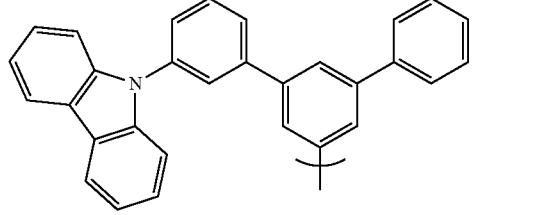
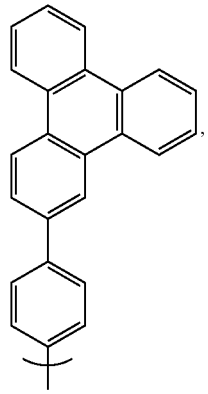,
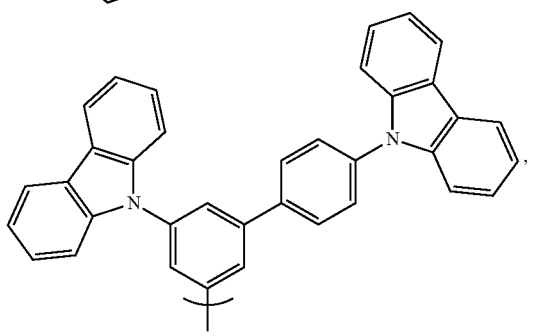
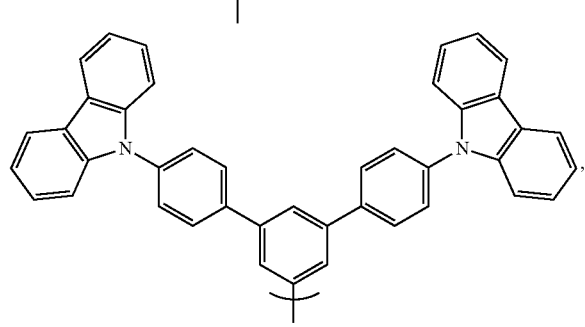
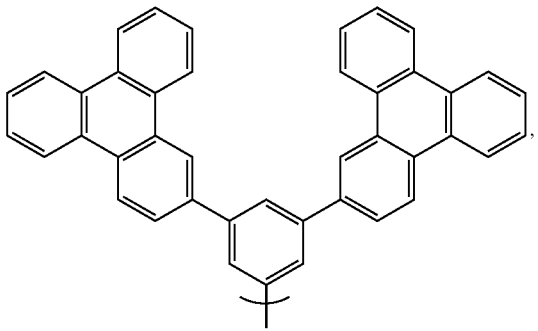

43
-continued
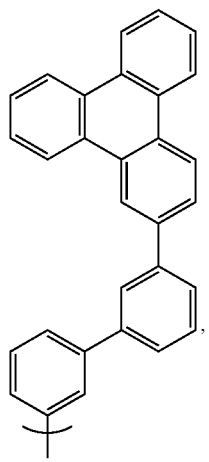
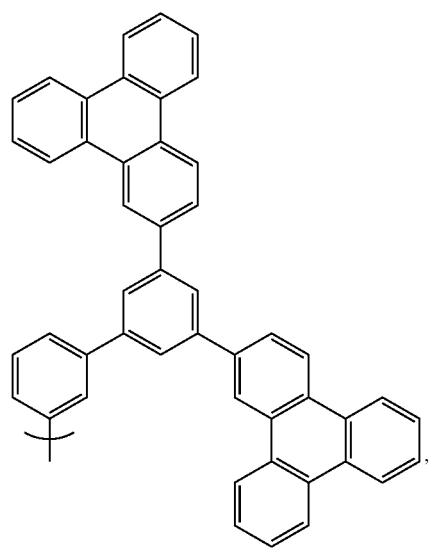
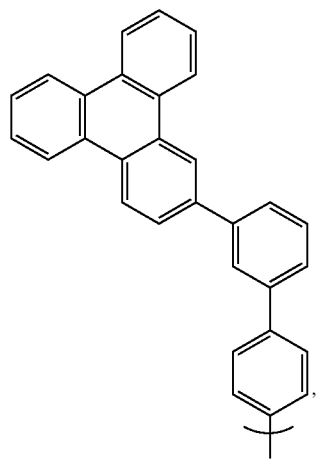
44
-continued
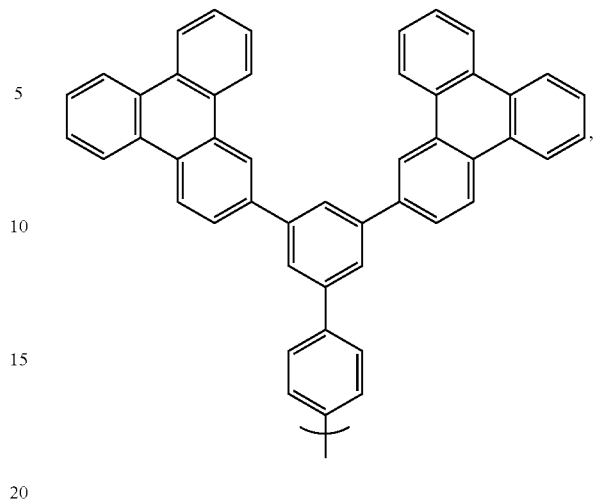
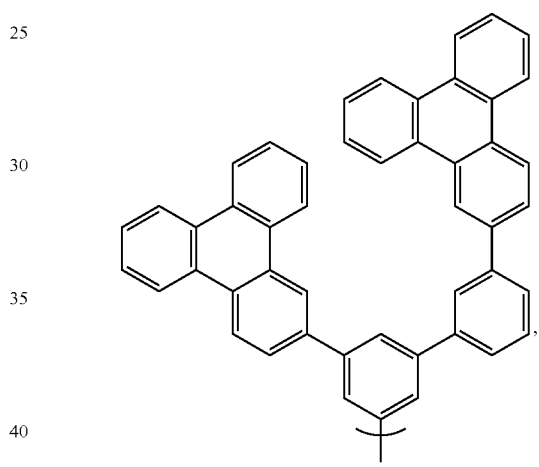
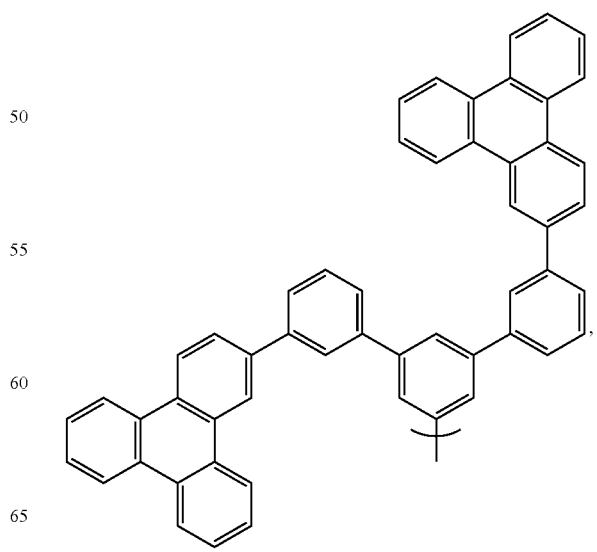

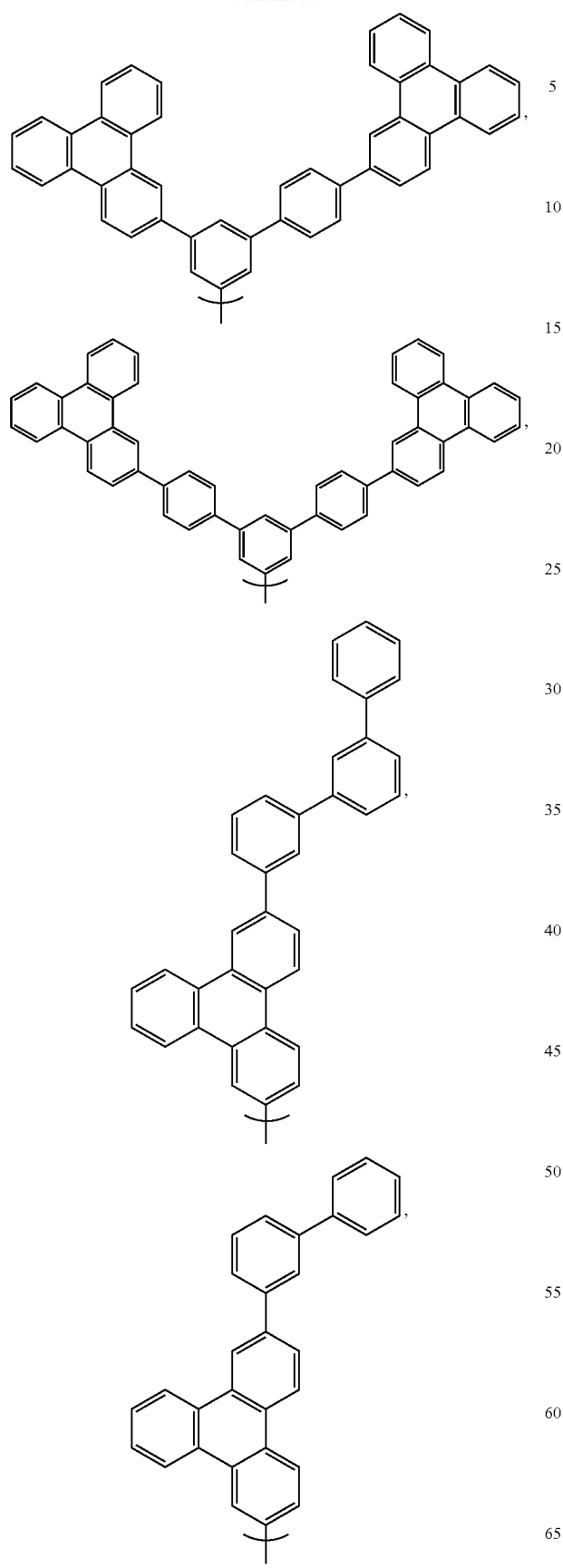
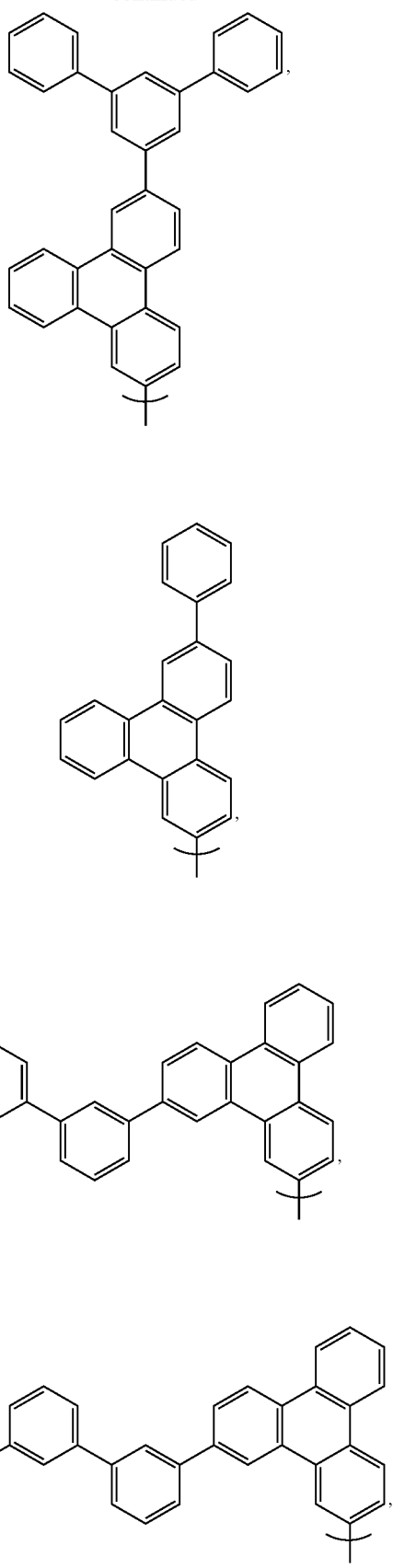

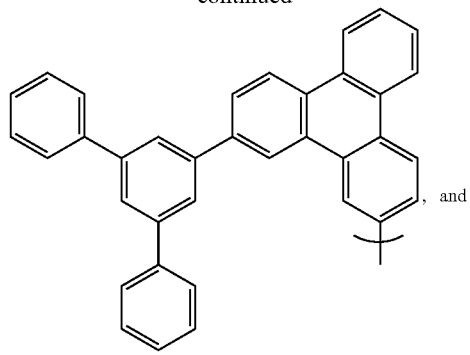, and
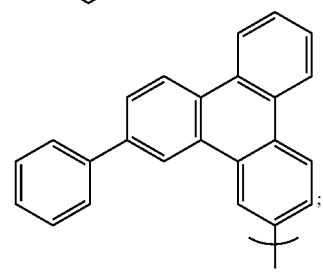;
wherein Group Z consists of:
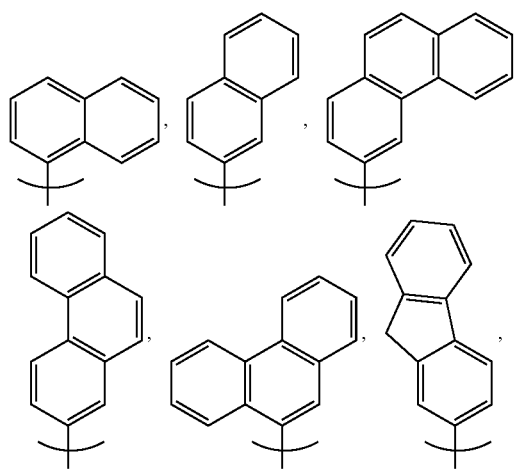
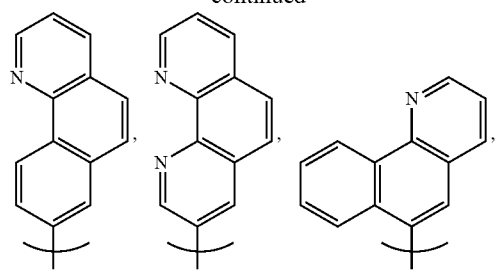
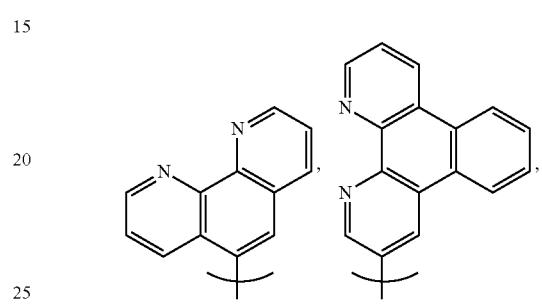
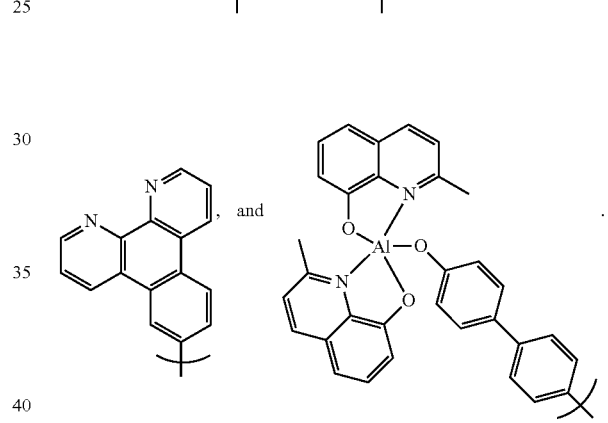
18. The organometallic compound of claim 1, wherein the organometallic compound is selected from the group consisting of:
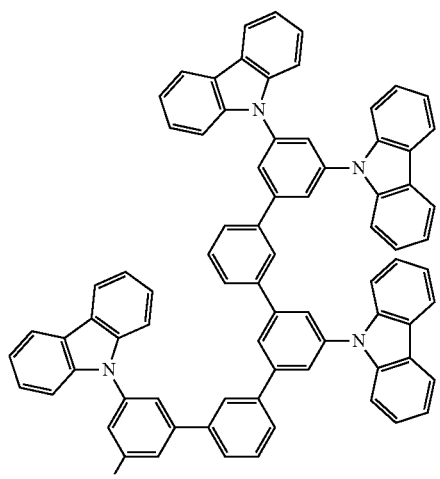

-continued
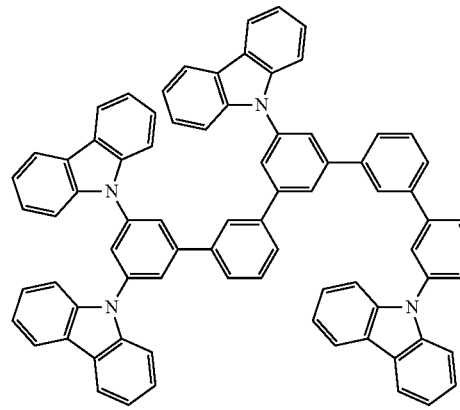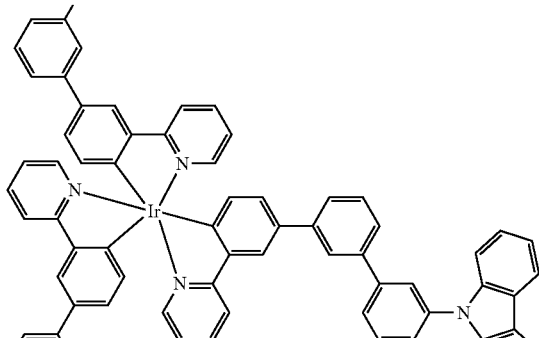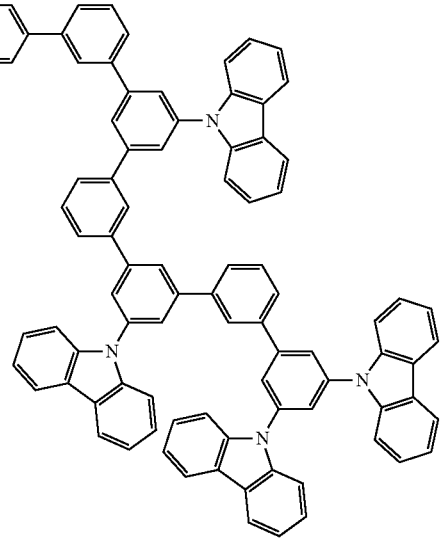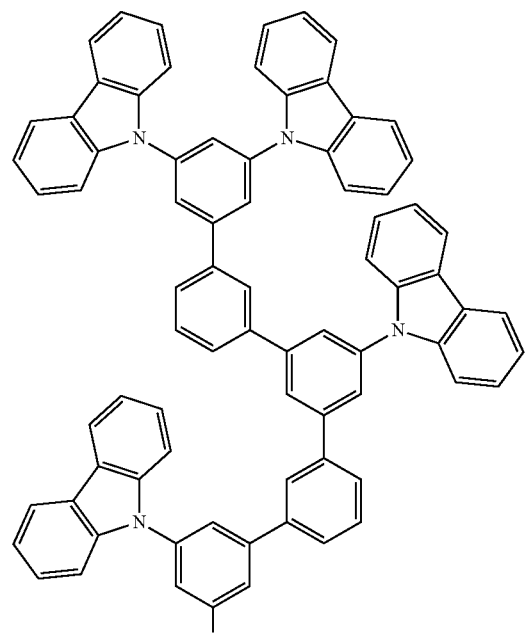

-continued
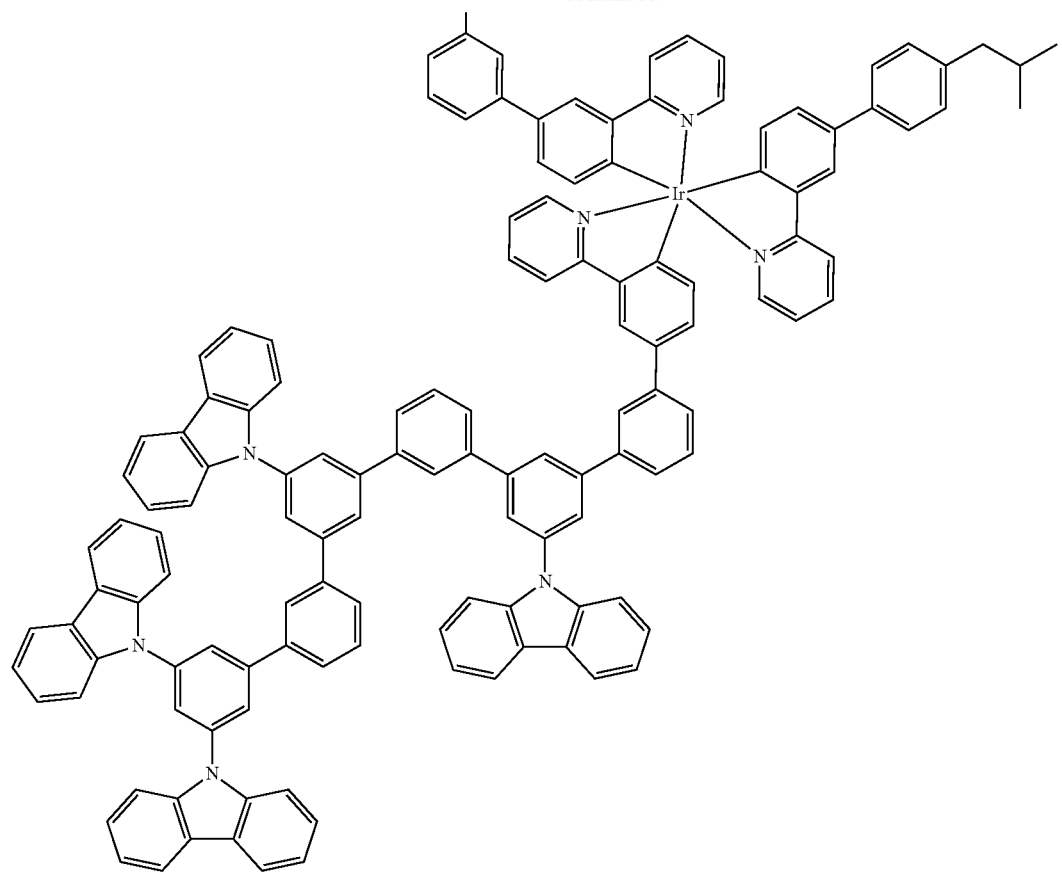
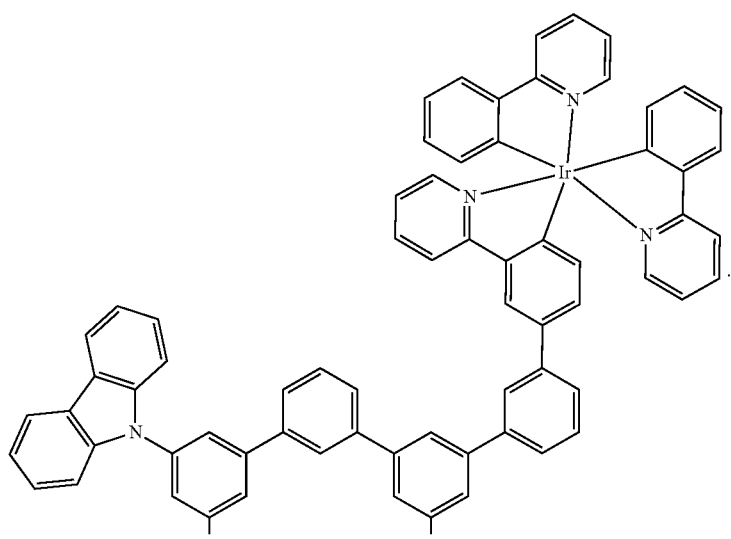

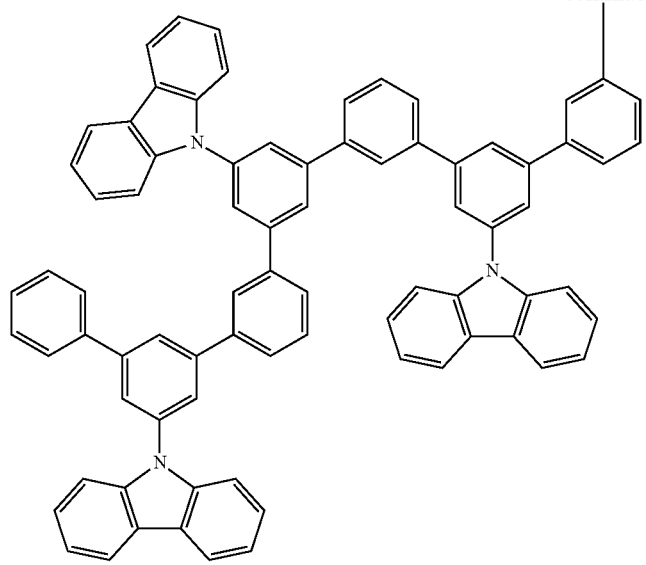
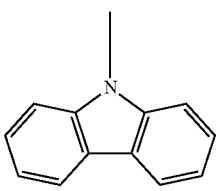

19. An organic electronic device comprising:
an anode;
a cathode; and
a first organic layer disposed between the anode and the cathode, wherein the first organic layer comprises an organometallic compound having the formula:

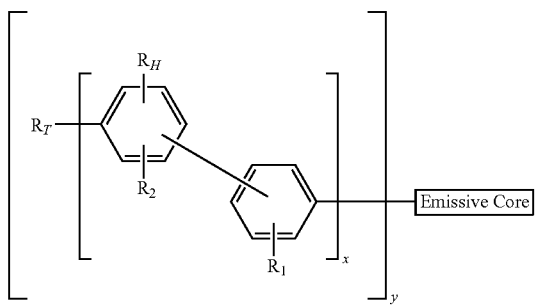

wherein the emissive core comprises a metal atom and a plurality of ligands coordinated to the metal atom;
wherein each branch is linked to one of the plurality of ligands;
wherein variable "y" has an integer value of 1 to 3;
wherein each variable "x" independently has an integer value of at least 2;
wherein each host moiety $R_H$ is independently an aryl group having at least two rings or a heteroaryl group having at least two rings;
wherein each $R_T$ is an optional terminal group independently selected from the group consisting of: an alkyl group, a heteroalkyl group, an aryl group, and a heteroaryl group;
wherein each of $R_1$ and $R_2$ represents one or more optional independently selected substitutions located on any position of their respective rings, wherein each of the substitutions are independently an alkyl group or a heteroalkyl group.

20. The device of claim 19, wherein the first organic layer is an electroluminescent layer.

21. The device of claim 20, wherein the first organic layer further comprises a host material that is separate and distinct from the organometallic compound.

22. The device of claim 19, wherein the device is an organic light-emitting device.

23. The device of claim 19, wherein the first organic layer is formed by solution processing.

24. The device of claim 19, further comprising a second organic layer disposed between the first organic layer and the anode, wherein the second organic layer comprises a hole injection material.

25. The device of claim 24, further comprising a third organic layer disposed between the second organic layer and the first organic layer, wherein the third organic layer comprises a hole transport material.

26. The device of claim 25, further comprising a fourth organic layer disposed between the first organic layer and the cathode, wherein the fourth organic layer comprises an electron transport material.

27. The device of claim 26, further comprising a fifth organic layer disposed between the fourth organic layer and the cathode, wherein the fifth organic layer comprises an electron transport material.

28. A method for making an organic electronic device, comprising:
providing a first electrode disposed on a substrate;
forming a first organic layer over the first electrode, wherein the first organic layer comprises an organometallic compound of claim 1; and
forming a second electrode disposed over the first organic layer.

29. The method of claim 28, wherein forming the first organic layer comprises depositing the organometallic compound by solution processing.

30. The method of claim 28, further comprising forming a second organic layer over the first electrode such that the second organic layer is disposed between the first organic layer and the first electrode.

31. The method of claim 30, wherein forming the second organic layer comprises depositing by solution processing.

32. The method of claim 30, wherein the second organic layer comprises a hole injection material.

33. The method of claim 31, further comprising cross-linking the second organic layer.

34. The method of claim 30, further comprising forming a third organic layer over the second organic layer such that the third organic layer is disposed between the second organic layer and the first organic layer, wherein the third organic layer comprises a hole transport material.

35. The method of claim 34, wherein forming the third organic layer comprises depositing by solution processing.

36. The method of claim 35, further comprising cross-linking the third organic layer.

37. The method of claim 34, further comprising depositing a fourth organic layer over the first organic layer such that the fourth organic layer is disposed between the first organic layer and the cathode, wherein the fourth organic layer comprises an electron transport material.

38. The method of claim 37, wherein the fourth organic layer is deposited by vacuum thermal evaporation.

39. The method of claim 37, further comprising depositing a fifth organic layer over the fourth organic layer such that the fifth organic layer is disposed between the fourth organic layer and the cathode, wherein the fifth organic layer comprises an electron transport material.

* * * * *